(12) United States Patent
Saunier

(10) Patent No.: US 7,488,355 B2
(45) Date of Patent: *Feb. 10, 2009

(54) COMPOSITION FOR DYEING KERATIN FIBERS, COMPRISING A DIAMINO-N,N-DIHYDROPYRAZOLONE COMPOUND, A COUPLER, AND A POLYOL

(75) Inventor: Jean-Baptiste Saunier, Paris (FR)

(73) Assignee: L'Oreal S.A., Paris (FR)

( * ) Notice: Subject to any disclaimer, the term of this patent is extended or adjusted under 35 U.S.C. 154(b) by 30 days.

This patent is subject to a terminal disclaimer.

(21) Appl. No.: 11/443,273

(22) Filed: May 31, 2006

(65) Prior Publication Data

US 2006/0277691 A1    Dec. 14, 2006

Related U.S. Application Data

(60) Provisional application No. 60/689,062, filed on Jun. 10, 2005.

(30) Foreign Application Priority Data

May 31, 2005    (FR)    ................................. 05 51445

(51) Int. Cl.
| | | |
|---|---|---|
| *A61Q 5/10* | (2006.01) | |
| *A01N 43/56* | (2006.01) | |
| *C07D 231/44* | (2006.01) | |

(52) U.S. Cl. ...................... 8/405; 8/406; 8/407; 8/408; 8/410; 8/411; 8/412; 8/421; 8/567; 514/406; 514/407; 548/369.1

(58) Field of Classification Search ..................... 8/405, 8/406, 407, 408, 410, 411, 412, 421, 567; 514/406, 407; 548/369.1

See application file for complete search history.

(56) References Cited

U.S. PATENT DOCUMENTS

| | | | |
|---|---|---|---|
| 3,649,158 | A | 3/1972 | Kalopissis |
| 4,003,699 | A | 1/1977 | Rose et al. |
| 4,128,425 | A | 12/1978 | Greenwald |
| RE30,199 | E | 1/1980 | Rose et al. |
| 4,314,808 | A | 2/1982 | Jacquet et al. |
| 4,823,985 | A | 4/1989 | Grollier et al. |
| 5,061,289 | A | 10/1991 | Clausen et al. |
| 5,089,025 | A | 2/1992 | Rose et al. |
| 5,380,340 | A | 1/1995 | Neunhoeffer et al. |
| 5,534,267 | A | 7/1996 | Neunhoeffer et al. |
| 5,663,366 | A | 9/1997 | Neunhoeffer et al. |
| 5,708,151 | A | 1/1998 | Möckli |
| 5,752,984 | A | 5/1998 | Knuebel et al. |
| 5,766,576 | A | 6/1998 | Löwe et al. |
| 5,865,855 | A | 2/1999 | Doehling et al. |
| 5,931,973 | A | 8/1999 | Malle et al. |
| 6,022,379 | A | 2/2000 | Genard et al. |
| 6,099,592 | A | 8/2000 | Vidal et al. |
| 6,099,593 | A | 8/2000 | Terranova et al. |
| 6,284,003 | B1 | 9/2001 | Rose et al. |
| 6,338,741 | B1 | 1/2002 | Vidal et al. |
| 6,391,064 | B1 | 5/2002 | Baudry et al. |
| 6,407,260 | B1 | 6/2002 | Bonaventure et al. |
| 6,432,146 | B1 | 8/2002 | Rondeau |
| 6,464,731 | B1 | 10/2002 | Genet et al. |
| 6,645,258 | B2 | 11/2003 | Vidal et al. |
| 6,692,538 | B2 | 2/2004 | Bonaventure et al. |
| 6,712,861 | B2 | 3/2004 | Rondeau |
| 6,730,789 | B1 | 5/2004 | Birault et al. |
| 6,773,463 | B2 | 8/2004 | Pasquier et al. |
| 6,884,265 | B2 | 4/2005 | Vidal et al. |
| 6,893,471 | B2 | 5/2005 | Vidal |
| 7,001,436 | B2 | 2/2006 | Vidal et al. |
| 7,285,137 | B2 * | 10/2007 | Vidal et al. ..................... 8/405 |
| 2001/0023514 | A1 | 9/2001 | Cottard et al. |
| 2003/0074747 | A1 * | 4/2003 | Vuarier et al. .................. 8/406 |
| 2003/0124079 | A1 | 7/2003 | Mougin et al. |
| 2003/0172475 | A1 | 9/2003 | Desenne et al. |
| 2004/0060126 | A1 | 4/2004 | Cottard et al. |
| 2004/0141943 | A1 | 7/2004 | Mougin et al. |
| 2004/0194228 | A1 | 10/2004 | Lagrange |
| 2004/0194229 | A1 | 10/2004 | Lagrange |
| 2004/0200009 | A1 | 10/2004 | Vidal |
| 2005/0000037 | A1 | 1/2005 | Audousset |
| 2005/0008594 | A1 | 1/2005 | Plos et al. |
| 2005/0039268 | A1 | 2/2005 | Plos et al. |
| 2005/0060815 | A1 | 3/2005 | Kravtchenko et al. |
| 2005/0076458 | A1 | 4/2005 | Cottard et al. |
| 2005/0166335 | A1 | 8/2005 | Vidal et al. |
| 2005/0183211 | A1 | 8/2005 | Samain et al. |
| 2005/0204483 | A1 | 9/2005 | Samain et al. |
| 2006/0070191 | A1 | 4/2006 | Lang et al. |

FOREIGN PATENT DOCUMENTS

| | | |
|---|---|---|
| DE | 16 17 893 | 6/1971 |
| DE | 23 59 399 | 6/1975 |
| DE | 38 25 212 | 2/1990 |
| DE | 38 43 892 | 6/1990 |
| DE | 41 33 957 | 4/1993 |

(Continued)

OTHER PUBLICATIONS

English Language Derwent Abstract for DE 101 18 271 (2002).

(Continued)

*Primary Examiner*—Eisa B Elhilo
(74) *Attorney, Agent, or Firm*—Finnegan, Henderson, Farabow, Garrett & Dunner LLP

(57) ABSTRACT

The present disclosure relates to a composition for dyeing keratin fibers, for instance human keratin fibers such as the hair, comprising at least one oxidation base chosen from diamino-N,N-dihydropyrazolone compounds and addition salts thereof, at least one coupler and at least one $C_4$-$C_{30}$ polyol. The present disclosure also relates to the dyeing process and kit using the composition as presently disclosed. Use of the present disclosure makes it, for example, possible to obtain fast coloration of keratin fibers that is resistant to light and to washing.

29 Claims, No Drawings

FOREIGN PATENT DOCUMENTS

| | | |
|---|---|---|
| DE | 42 34 885 | 4/1994 |
| DE | 44 04 564 | 8/1995 |
| DE | 195 43 988 | 5/1997 |
| DE | 197 30 412 | 12/1998 |
| DE | 101 18 271 | 3/2002 |
| DE | 201 04 441 | 7/2002 |
| DE | 101 48 847 | 4/2003 |
| EP | 0 173 109 | 3/1986 |
| EP | 0 714 954 | 6/1996 |
| EP | 0 770 375 | 5/1997 |
| EP | 0 984 010 | 3/2000 |
| EP | 1 025 834 | 8/2000 |
| EP | 1 166 753 | 1/2002 |
| EP | 1 166 754 | 1/2002 |
| EP | 1 170 000 | 1/2002 |
| EP | 1 170 001 | 1/2002 |
| EP | 1 197 203 | 4/2002 |
| EP | 1 437 123 | 7/2004 |
| EP | 1 464 327 | 10/2004 |
| EP | 1 473 023 | 11/2004 |
| EP | 1 550 656 | 7/2005 |
| EP | 1 598 047 | 11/2005 |
| FR | 1 584 111 | 12/1969 |
| FR | 2 456 764 | 12/1980 |
| FR | 2 586 913 | 3/1987 |
| FR | 2 733 749 | 11/1996 |
| FR | 2 746 392 | 9/1997 |
| FR | 2 750 048 | 12/1997 |
| FR | 2 760 010 | 8/1998 |
| FR | 2 782 452 | 2/2000 |
| FR | 2 788 273 | 7/2000 |
| FR | 2 798 931 | 3/2001 |
| FR | 2 801 308 | 5/2001 |
| FR | 2 803 195 | 7/2001 |
| FR | 2 811 993 | 1/2002 |
| FR | 2 817 467 | 6/2002 |
| FR | 2 822 696 | 10/2002 |
| FR | 2 825 622 | 12/2002 |
| FR | 2 825 625 | 12/2002 |
| FR | 2 825 702 | 12/2002 |
| FR | 2 825 703 | 12/2002 |
| FR | 2 833 834 | 6/2003 |
| FR | 2 845 387 | 4/2004 |
| FR | 2 848 837 | 6/2004 |
| FR | 2 848 840 | 6/2004 |
| FR | 2 855 966 | 12/2004 |
| FR | 2 855 967 | 12/2004 |
| GB | 1 026 978 | 4/1966 |
| GB | 1 153 196 | 5/1969 |
| GB | 1 213 697 | 11/1970 |
| JP | 2-19576 | 1/1990 |
| JP | 5-163124 | 6/1993 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |
| WO | WO 02/22093 | 3/2002 |

OTHER PUBLICATIONS

English Language Derwent Abstract for DE 101 48 847 (2003).
English Language Derwent Abstract for DE 201 04 441 (2002).
English Language Derwent Abstract for EP 0 770 375 (1997).
English Language Derwent Abstract for EP 1 197 203 (2002).
English Language Derwent Abstract for FR 2 456 764 (1980).
English Language Derwent Abstract for JP 2-19576 (1990).
English Language Derwent Abstract for JP 5-163124 (1993).
Co-pending U.S. Appl. No. 11/443,274, Title: Composition for Dyeing Keratin Fibers, Comprising at Least One Diamino-N,N-Dihydropyrazolone Derivative, at Least One Coupler, and at Least One Surfactant Inventors: Jean-Baptiste Saunier U.S. Filing Date: May 31, 2006.
Co-pending U.S. Appl. No. 11/443,353, Title: Composition for Dyeing Keratin Fibers, Comprising at Least One Diamino-N,N-Dihydropyrazolone Derivative, at Least One Coupler and at Least One Associative Polyurethane Polymer Inventors: Jean-Baptiste Saunier U.S. Filing Date: May 31, 2006.
Co-pending U.S. Appl. No. 11/442,967, Title: Composition for Dyeing Keratin Fibers, Comprising at Least One Diamino-N,N-Dihydropyrazolone Derivative, at Least One Coupler, and at Least One Heterocyclic Direct Dye Inventors: Leila Hercouet U.S. Filing Date: May 31, 2006.
European Search Report for EP 06 11 4654, mailed Aug. 23, 2006 (corresponding to the present application).
European Search Report for EP 06 11 4652, mailed Aug. 23, 2006 (corresponding to U.S. Appl. No. 11/443,274).
European Search Report for EP 06 11 4656, mailed Sep. 22, 2006 (corresponding to U.S. Appl. No. 11/443,353).
European Search Report for EP 06 11 4655, mailed Sep. 22, 2006 (corresponding to U.S. Appl. No. 11/442,967).
French Report for FR 05 51445, mailed Feb. 6, 2006 (corresponding to the present application).
French Report for FR 05 51444, mailed Feb. 6, 2006 (corresponding to U.S. Appl. No. 11/443,274).
French Report for FR 05 51429, mailed Feb. 1, 2006 (corresponding to U.S. Appl. No. 11/443,353).
French Report for FR 05 51446, mailed Feb. 1, 2006 (corresponding to U.S. Appl. No. 11/442,967).
Boros et al., *J. Het. Chem.*, 38(3): 613-616 (2001).
Cohen & Zand, *J. Am. Chem. Soc.*, 84: 586-590 (1962).
Fonnum et al., *Colloid Polym. Sci*, 271(4): 380-389 (1993).
Heyman & Snyder, *Tetrahedron. Letters*, 30: 2859-2862 (1973).
Kharasch & Bruice, *J. Am. Chem. Soc.*, 73: 3240-3244 (1951).
Lingens and Shneider-Bernlöhr, *Justus Liebig Ann. Chem.*, 686: 134-144 (1965).
Magnien & Baltzly, *J. Org. Chem.*, 23: 2029-2032 (1958).
Stenzl et al., *Helvetica Chimica Acta*, 33: 1183-1194 (1950).

\* cited by examiner

COMPOSITION FOR DYEING KERATIN FIBERS, COMPRISING A DIAMINO-N,N-DIHYDROPYRAZOLONE COMPOUND, A COUPLER, AND A POLYOL

CROSS-REFERENCE TO RELATED APPLICATIONS

This application claims benefit of U.S. Provisional Application No. 60/689,062, filed Jun. 10, 2005, the contents of which are incorporated herein by reference. This application also claims benefit of priority under 35 U.S.C. § 119 to French Patent Application No. FR 05 51445, filed May 31, 2005, the contents of which are also incorporated herein by reference.

FIELD OF THE INVENTION

The present disclosure relates to a composition for dyeing keratin fibers, for instance human keratin fibers such as the hair, comprising at least one oxidation base chosen from diamino-N,N-dihydropyrazolone compounds and addition salts thereof, at least one coupler and at least one $C_4$-$C_{30}$ polyol, and also to the dyeing process using such a composition.

BACKGROUND OF THE INVENTION

It is known practice to dye keratin fibers, for instance human keratin fibers such as the hair, with dye compositions comprising oxidation dye precursors, for example ortho- or para-phenylenediamines, ortho- or para-aminophenols, and heterocyclic compounds such as diaminopyrazole derivatives, pyrazolo[1,5-a]pyrimidine derivatives, pyrimidine derivatives, pyridine derivatives, indole derivatives and indoline derivatives, which are generally known as oxidation bases. Oxidation dye precursors, or oxidation bases, are colorless or weakly colored compounds that, when combined with oxidizing products, can give rise to colored compounds and dyes via a process of oxidative condensation. Permanent colorations are thus obtained.

It is also known that the shades obtained with these oxidation bases may be varied by combining them with couplers or coloration modifiers, the latter being chosen, for example, from meta-phenylenediamines, meta-aminophenols, meta-hydroxyphenols and certain heterocyclic compounds.

The variety of molecules used with respect to the oxidation bases and couplers allows a wide range of colors to be obtained.

The use of oxidation bases such as para-phenylenediamine and para-aminophenol derivatives allows a quite broad range of colors to be obtained at basic pH without, however, achieving shades with good chromaticity, while at the same time giving the hair at least one excellent property in terms of strength of color, variety of shades, uniformity of the color and/or fastness with respect to external agents.

The use of these bases at neutral pH may not allow a varied range of shades to be produced, in particular for warm shades such as reds and oranges.

SUMMARY OF THE INVENTION

It would thus be desirable to provide novel compositions for dyeing keratin fibers that make it possible to obtain a strong, chromatic, aesthetic and or sparingly selective coloration in varied shades, which shows good resistance to at least one of the various attacking factors to which the hair may be subjected, such as shampoo, light, sweat and permanent reshaping operations.

DETAILED DESCRIPTION OF THE INVENTION

One aspect of the present disclosure is thus a composition for dyeing keratin fibers, comprising, in a suitable medium:
at least one oxidation base chosen from diamino-N,N-dihydropyrazolone compounds of formula (I) and addition salts thereof:

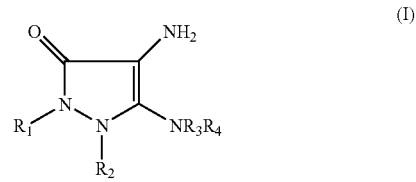

in which:
$R^1$, $R_2$, $R_3$ and $R_4$, which may be identical or different, are chosen from:
linear or branched $C_1$-$C_{10}$, for example, $C_1$-$C_6$, alkyl radicals optionally substituted with at least at least one radical chosen from radicals $OR_5$, radicals $NR_6R_7$, carboxyl radicals, sulfonic radicals, carboxamido radicals $CONR_6R_7$, sulfonamido radicals $SO_2NR_6R_7$, heteroaryl or aryl radiclas optionally substituted with at least one group chosen from at least one ($C_1$-$C_4$)alkyl, hydroxyl, $C_1$-$C_2$ alkoxy, amino and (di)($C_1$-$C_2$)alkylamino groups;
aryl radicals optionally substituted with at least at least one radica chosen from ($C_1$-$C_4$)alkyl, hydroxyl, $C_1$-$C_2$ alkoxy, amino and (di)($C_1$-$C_2$)alkylamino radicals;
5- or 6-membered heteroaryl radicals, optionally substituted with at least at least one radical chosen from ($C_1$-$C_4$)alkyl and ($C_1$-$C_2$)alkoxy radicals;
$R_3$ and $R_4$ may also each be a hydrogen atom;
$R_5$, $R_6$ and $R_7$, which may be identical or different, are chosen from:
hydrogen atoms;
linear or branched $C_1$-$C_4$ alkyl radicals optionally substituted with at least at least one radical chosen from hydroxyl, $C_1$-$C_2$ alkoxy, carboxamido $CONR_8R_9$, sulfonyl $SO_2R_8$ and aryl radicals optionally substituted with at least one radical chosen from ($C_1$-$C_4$)alkyl, hydroxyl, $C_1$-$C_2$ alkoxy, amino and (di)($C_1$-$C_2$)alkylamino radicals; aryl optionally substituted with at least one radical chosen from ($C_1$-$C_4$)alkyl, hydroxyl, $C_1$-$C_2$ alkoxy, amino and (di)($C_1$-$C_2$)alkylamino radicals;
$R_6$ and $R_7$, which may be identical or different, may also each independently be chosen from carboxamido radicals $CONR_8R_9$; and sulfonyl radicals $SO_2R_8$;
$R_8$ and $R_9$, which may be identical or different, are chosen from hydrogen atoms; linear or branched $C_1$-$C_4$ alkyl radicals optionally substituted with at least at least one radical chosen from hydroxyl and $C_1$-$C_2$ alkoxy radicals;
$R_1$ and $R_2$, on the one hand, and $R_3$ and $R_4$, on the other hand, may form, with the nitrogen atom(s) to which they are attached, a saturated or unsaturated 5- to 7-membered heterocycle optionally substituted with at least at least one entity chosen from halogen atoms and from amino, (di)($C_1$-$C_4$) alkylamino, hydroxyl, carboxyl, carboxamido and ($C_1$-$C_2$) alkoxy radicals, and $C_1$-$C_4$ alkyl radicals optionally substituted with at least one radical chosen from at least one hydroxyl, amino, (di)alkylamino, alkoxy, carboxyl and sulfonyl radicals;

$R_3$ and $R_4$ may also form, together with the nitrogen atom to which they are attached, a 5- or 7-membered heterocycle, the carbon atoms of which may be replaced with an oxygen or optionally substituted nitrogen atom;
  at least one coupler; and
  at least one $C_4$-$C_{30}$ polyol.

The present disclosure surprisingly, and unexpectedly makes it possible for instance to obtain a strong, aesthetic, and/or sparingly selective coloration of keratin fibers in varied shades, which shows good resistance to the various attacking factors to which the hair may be subjected, such as shampoo, light, sweat and permanent reshaping operations. It furthermore makes it possible to obtain intense and varied colorations at neutral pH.

Another aspect of the present disclosure is a process for dyeing keratin fibers using the composition as disclosed herein, and also the use of this composition for dyeing keratin fibers.

Finally, another aspect of the present disclosure is a dyeing kit comprising, on the one hand, a dye composition comprising at least one oxidation base of formula (I), at least one coupler and at least one $C_4$-$C_{30}$ polyol, and, on the other hand, a composition comprising at least one oxidizing agent.

In the context of the present disclosure, the term "alkyl radical" means linear or branched alkyl radicals which are $C_1$-$C_{10}$ unless otherwise indicated, for example $C_1$-$C_6$ and further, for example, $C_1$-$C_4$, such methyl, ethyl, propyl, isopropyl, isobutyl, tert-butyl, pentyl and hexyl.

In at least one embodiment, in formula (I), the radicals $R_1$ and $R_2$, which may be identical or different, are chosen from:
  $C_1$-$C_6$ alkyl radicals optionally substituted with at least one radical chosen from hydroxyl, ($C_1$-$C_2$)alkoxy, amino and (di)($C_1$-$C_2$)alkylamino radicals;
  phenyl, methoxyphenyl, ethoxyphenyl and benzyl radicals.

For example, in at least one embodiment, the radicals $R_1$ and $R_2$, which may be identical or different, are chosen from methyl, ethyl, 2-hydroxyethyl, 3-hydroxypropyl, 2-hydroxypropyl and phenyl radicals.

According to another embodiment, the radicals $R_1$ and $R_2$ form, together with the nitrogen atoms to which they are attached, a saturated or unsaturated, optionally substituted 5- or 6-membered ring.

According to yet another embodiment, the radicals $R_1$ and $R_2$ form, together with the nitrogen atoms to which they are attached, a pyrazolidine or pyridazolidine ring, optionally substituted with at least at least one $C_1$-$C_4$ alkyl, hydroxyl, ($C_1$-$C_2$)alkoxy, carboxyl, carboxamido, amino and (di)($C_1$-$C_2$)alkylamino radicals.

And, in at least one embodiment, the radicals $R_1$ and $R_2$ form, together with the nitrogen atoms to which they are attached, a pyrazolidine or pyridazolidine ring.

In at least one embodiment, the radicals $R_3$ and $R_4$, which may be identical or different, are chosen from hydrogen atoms; and from linear or branched $C_1$-$C_6$ alkyl radicals optionally substituted with at least at least one radical chosen from hydroxyl, ($C_1$-$C_2$)alkoxy, amino and (di)($C_1$-$C_2$)alkylamino radicals; phenyl radicals optionally substituted with at least at least one radical chosen from hydroxyl, amino and ($C_1$-$C_2$)alkoxy radicals.

For instance, according to at least one embodiment, the radicals $R_3$ and $R_4$, which may be identical or different, are chosen from hydrogen and from methyl, ethyl, isopropyl, 2-hydroxyethyl, 3-hydroxypropyl, 2-hydroxypropyl and 2-carboxyethyl radicals. For example, according to at least one embodiment, the radicals $R_3$ and $R_4$ are each a hydrogen atom.

According to another embodiment, the radicals $R_3$ and $R_4$ form, together with the nitrogen atom to which they are attached, a 5- or 7-membered ring chosen from pyrrolidine, piperidine, homopiperidine, piperazine and homopiperazine heterocycles; the rings possibly being substituted with at least one radical chosen from hydroxyl, amino, (di)($C_1$-$C_2$)alkylamino, carboxyl, carboxamido and $C_1$-$C_4$ alkyl radicals optionally substituted with at least one radical chosen from hydroxyl, amino and $C_1$-$C_2$ (di)alkylamino radicals.

For instance, according to another embodiment, the radicals $R_3$ and $R_4$ form, together with the nitrogen atom to which they are attached, a 5- or 7-membered ring chosen from pyrrolidine, 2,5-dimethylpyrrolidine, pyrrolidine-2-carboxylic acid, 3-hydroxypyrrolidine-2-carboxylic acid, 4-hydroxypyrrolidine-2-carboxylic acid, 2,4-dicarboxypyrrolidine, 3-hydroxy-2-hydroxymethylpyrrolidine, 2-carboxamidopyrrolidine, 3-hydroxy-2-carboxamidopyrrolidine, 2-(diethylcarboxamido)pyrrolidine, 2-hydroxymethylpyrrolidine, 3,4-dihydroxy-2-hydroxymethylpyrrolidine, 3-hydroxypyrrolidine, 3,4-dihydroxypyrrolidine, 3-aminopyrrolidine, 3-methylaminopyrrolidine, 3-dimethylaminopyrrolidine, 4-amino-3-hydroxypyrrolidine, 3-hydroxy4-(2-hydroxyethyl)aminopyrrolidine, piperidine, 2,6-dimethylpiperidine, 2-carboxypiperidine, 2-carboxamidopiperidine, 2-hydroxymethylpiperidine, 3-hydroxy-2-hydroxymethylpiperidine, 3-hydroxypiperidine, 4-hydroxypiperidine, 3-hydroxymethyl-piperidine, homopiperidine, 2-carboxyhomopiperidine, 2-carboxamidohomopiperidine, homopiperazine, N-methylhomopiperazine and N-(2-hydroxyethyl)homopiperazine.

In another embodiment as disclosed herein, the radicals $R_3$ and $R_4$ form, together with the nitrogen atom to which they are attached, a 5- or 7-membered ring chosen from pyrrolidine, 3-hydroxypyrrolidine, 3-aminopyrrolidine, 3-dimethylaminopyrrolidine, pyrrolidine-2-carboxylic acid, 3-hydroxypyrrolidine-2-carboxylic acid, piperidine, hydroxypiperidine, homopiperidine, diazepane, N-methylhomopiperazine and N-β-hydroxyethylhomopiperazine.

In accordance with at least one embodiment of the present disclosure, for example, the radicals $R_3$ and $R_4$ form, together with the nitrogen atom to which they are attached, a 5-membered ring such as pyrrolidine, 3-hydroxypyrrolidine, 3-aminopyrrolidine or 3-dimethylaminopyrrolidine.

The compounds of formula (I) may be optionally salified with strong mineral acids, for instance HCl, HBr, HI, $H_2SO_4$ or $H_3PO_4$, or organic acids, for instance acetic acid, lactic acid, tartaric acid, citric acid or succinic acid, benzenesulfonic acid, para-toluenesulfonic acid, formic acid or methanesulfonic acid.

They may also be in the form of solvates, for example a hydrate or a solvate of a linear or branched alcohol such as ethanol or isopropanol.

Examples of derivatives of formula (I) that may be mentioned include, but are not limited to, the compounds presented below, or the addition salts thereof:

4,5-diamino-1,2-dimethyl-1,2-dihydropyrazol-3-one;

4-amino-5-methylamino-1,2-dimethyl-1,2-dihydropyrazol-3-one;

4-amino-5-dimethylamino-1,2-dimethyl-1,2-dihydropyrazol-3-one;

4-amino-5-(2-hydroxyethyl)amino-1,2-dimethyl-1,2-dihydropyrazol-3-one;

4-amino-5-(pyrrolidin-1-yl)-1,2-dimethyl-1,2-dihydropyrazol-3-one;

4-amino-5-(piperid-1-yl)-1,2-dimethyl-1,2-dihydropyrazol-3-one;

4,5-diamino-1,2-di(2-hydroxyethyl)-1,2-dihydropyrazol-3-one;
4-amino-5-methylamino-1,2-di(2-hydroxyethyl)-1,2-dihydropyrazol-3-one;
4-amino-5-dimethylamino-1,2-di(2-hydroxyethyl)-1,2-dihydropyrazol-3-one;
4-amino-5-(2-hydroxyethyl)amino-1,2-di(2-hydroxyethyl)-1,2-dihydropyrazol-3-one;
4-amino-5-(pyrrolidin-1-yl)-1,2-di(2-hydroxyethyl)-1,2-dihydropyrazol-3-one;
4-amino-5-(piperid-1-yl)-1,2-di(2-hydroxyethyl)-1,2-dihydropyrazol-3-one;
4,5-diamino-1,2-diethyl-1,2-dihydropyrazol-3-one;
4,5-diamino-1,2-phenyl-1,2-dihydropyrazol-3-one;
4,5-diamino-1-ethyl-2-methyl-1,2-dihydropyrazol-3-one;
4,5-diamino-2-ethyl-1-methyl-1,2-dihydropyrazol-3-one;
4,5-diamino-1-phenyl-2-methyl-1,2-dihydropyrazol-3-one;
4,5-diamino-2-phenyl-1-methyl-1,2-dihydropyrazol-3-one;
4,5-diamino-1-(2-hydroxyethyl)-2-methyl-1,2-dihydropyrazol-3-one;
4,5-diamino-2-(2-hydroxyethyl)-1-methyl-1,2-dihydropyrazol-3-one;
2,3-diamino-6,7-dihydro-1H,5H-pyrazolo[1,2-a]pyrazol-1-one;
2-amino-3-methylamino-6,7-dihydro-1H,5H-pyrazolo[1,2-a]pyrazol-1-one;
2-amino-3-dimethylamino-6,7-dihydro-1H,5H-pyrazolo[1,2-a]pyrazol-1-one;
2-amino-3-ethylamino-6,7-dihydro-1H,5H-pyrazolo[1,2-a]pyrazol-1-one;
2-amino-3-isopropylamino-6,7-dihydro-1H,5H-pyrazolo[1,2-a]pyrazol-1-one;
2-amino-3-(2-hydroxyethyl)amino-6,7-dihydro-1H,5H-pyrazolo[1,2-a]pyrazol-1-one;
2-amino-3-(2-hydroxypropyl)amino-6,7-dihydro-1H,5H-pyrazolo[1,2-a]pyrazol-1-one;
2-amino-3-bis(2-hydroxyethyl)amino-6,7-dihydro-1H,5H-pyrazolo[1,2-a]pyrazol-1-one;
2-amino-3-(pyrrolidin-1-yl)-6,7-dihydro-1H,5H-pyrazolo[1,2-a]pyrazol-1-one;
2-amino-3-(3-hydroxypyrrolidin-1-yl)-6,7-dihydro-1H,5H-pyrazolo[1,2-a]pyrazol-1-one;
2-amino-3-(piperid-1-yl)-6,7-dihydro-1H,5H-pyrazolo[1,2-a]pyrazol-1-one;
2,3-diamino-6-hydroxy-6,7-dihydro-1H,5H-pyrazolo[1,2-a]pyrazol-1-one;
2,3-diamino-6-methyl-6,7-dihydro-1H,5H-pyrazolo[1,2-a]pyrazol-1-one;
2,3-diamino-6-dimethyl-6,7-dihydro-1H,5H-pyrazolo[1,2-a]pyrazol-1-one;
2,3-diamino-5,6,7,8-tetrahydro-1H,6H-pyridazino[1,2-a]pyrazol-1-one;
2,3-diamino-5,8-dihydro-1H,6H-pyridazino[1,2-a]pyrazol-1-one;
4-amino-5-dimethylamino-1,2-diethyl-1,2-dihydropyrazol-3-one;
4-amino-1,2-diethyl-5-ethylamino-1,2-dihydropyrazol-3-one;
4-amino-1,2-diethyl-5-isopropylamino-1,2-dihydropyrazol-3-one;
4-amino-1,2-diethyl-5-(2-hydroxyethylamino)-1,2-dihydropyrazol-3-one;
4-amino-5-(2-dimethylaminoethylamino)-1,2-diethyl-1,2-dihydropyrazol-3-one;
4-amino-5-[bis(2-hydroxyethyl)amino]-1,2-diethyl-1,2-dihydropyrazol-3-one;
4-amino-1,2-diethyl-5-(3-imidazol-1-ylpropylamino)-1,2-dihydropyrazol-3-one;
4-amino-5-dimethylamino-1,2-diethyl-1,2-dihydropyrazol-3-one;
4-amino-1,2-diethyl-5-ethylamino-1,2-dihydropyrazol-3-one;
4-amino-1,2-diethyl-5-isopropylamino-1,2-dihydropyrazol-3-one;
4-amino-1,2-diethyl-5-(2-hydroxyethylamino)-1,2-dihydropyrazol-3-one;
4-amino-5-(2-dimethylaminoethylamino)-1,2-diethyl-1,2-dihydropyrazol-3-one;
4-amino-5-[bis(2-hydroxyethyl)amino]-1,2-diethyl-1,2-dihydropyrazol-3-one;
4-amino-1,2-diethyl-5-(3-imidazol-1-ylpropylamino)-1,2-dihydropyrazol-3-one;
4-amino-1,2-diethyl-5-(3-hydroxypyrrolidin-1-yl)-1,2-dihydropyrazol-3-one;
4-amino-1,2-diethyl-5-pyrrolidin-1-yl-1,2-dihydropyrazol-3-one;
4-amino-5-(3-dimethylaminopyrrolidin-1-yl)-1,2-diethyl-1,2-dihydropyrazol-3-one;
4-amino-1,2-diethyl-5-(4-methylpiperazin-1-yl)pyrazolidin-3-one;
2,3-diamino-6-hydroxy-6,7-dihydro-5H-pyrazolo[1,2-a]pyrazol-1-one;

some of which are given below to illustrate the names with chemical structures:

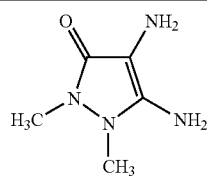
4,5-diamino-1,2-dimethyl-1,2-dihydropyrazol-3-one

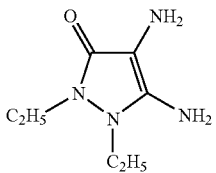
4,5-diamino-1,2-diethyl-1,2-dihydropyrazol-3-one

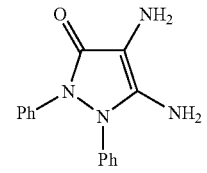
4,5-diamino-1,2-diphenyl-1,2-dihydropyrazol-3-one

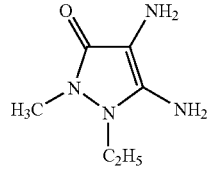
4,5-diamino-1-ethyl-2-methyl-1,2-dihydropyrazol-3-one

-continued

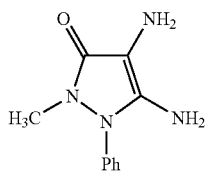 4,5-diamino-1-phenyl-2-methyl-1,2-dihydropyrazol-3-one

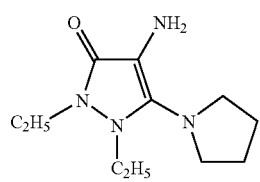 4-amino-5-(pyrrolidin-1-yl)-1,2-diethyl-1,2-dihydropyrazol-3-one

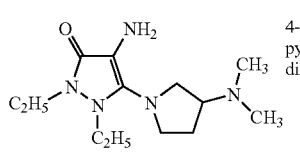 4-amino-5-(3-dimethylamino-pyrrolidin-1-yl)-1,2-diethyl-1,2-dihydropyrazol-3-one

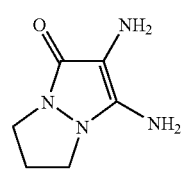 2,3-diamino-6,7-dihydro-1H,5H-pyrazolo[1,2-a]pyrazol-1-one

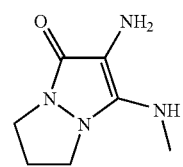 2-amino-3-methylamino-6,7-dihydro-1H,5H-pyrazolo[1,2-a]pyrazol-1-one

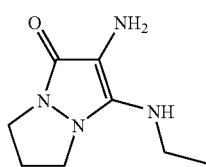 2-amino-3-ethylamino-6,7-dihydro-1H,5H-pyrazolo[1,2-a]pyrazol-1-one

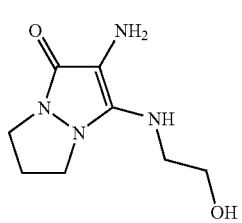 2-amino-3-(2-hydroxyethyl)amino-6,7-dihydro-1H,5H-pyrazolo[1,2-a]pyrazol-1-one

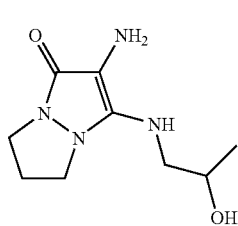 2-amino-3-(2-hydroxypropyl)amino-6,7-dihydro-1H,5H-pyrazolo[1,2-a]pyrazol-1-one -continued

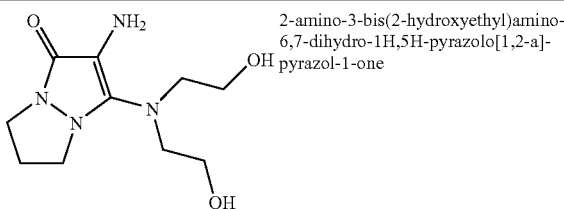 2-amino-3-bis(2-hydroxyethyl)amino-6,7-dihydro-1H,5H-pyrazolo[1,2-a]-pyrazol-1-one

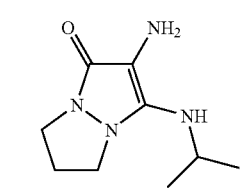 2-amino-3-isopropylamino-6,7-dihydro-1H,5H-pyrazolo[1,2-a]pyrazol-1-one

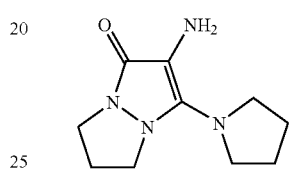 2-amino-3-(pyrrolidin-1-yl)-6,7-dihydro-1H,5H-pyrazolo[1,2-a]pyrazol-1-one

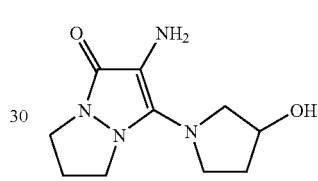 2-amino-3-(3-hydroxypyrrolidin-1-yl)-6,7-dihydro-1H,5H-pyrazolo[1,2-a]pyrazol-1-one

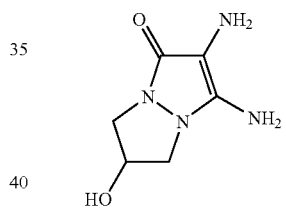 2,3-diamino-6-hydroxy-6,7-dihydro-1H,5H-pyrazolo[1,2-a]pyrazol-1-one

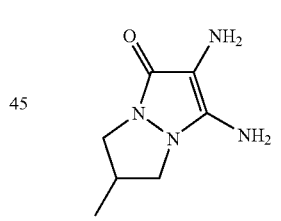 2,3-diamino-6-methyl-6,7-dihydro-1H,5H-pyrazolo[1,2-a]pyrazol-1-one

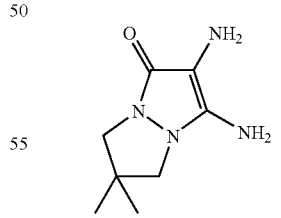 2,3-diamino-6,6-dimethyl-6,7-dihydro-1H,5H-pyrazolo[1,2-a]pyrazol-1-one

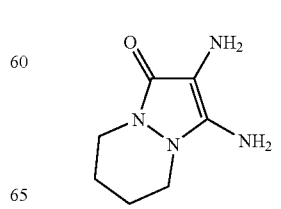 2,3-diamino-5,6,7,8-tetrahydro-1H,6H-pyridazino[1,2-a]pyrazol-1-one

-continued

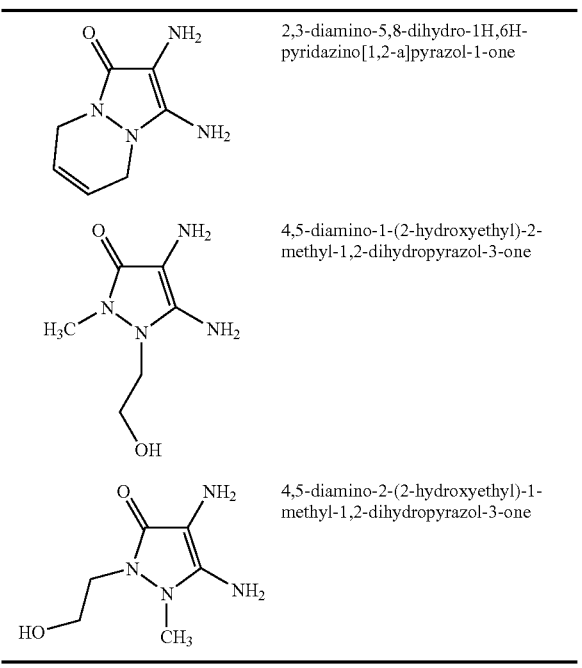

2,3-diamino-5,8-dihydro-1H,6H-pyridazino[1,2-a]pyrazol-1-one 4,5-diamino-1-(2-hydroxyethyl)-2-methyl-1,2-dihydropyrazol-3-one 4,5-diamino-2-(2-hydroxyethyl)-1-methyl-1,2-dihydropyrazol-3-one Among these compounds, the diamino-N,N-dihydropyrazolone compounds of formula (I), or the addition salts thereof, which may be used in at least one embodiment include, but are not limited to, the following:

2,3-diamino-6,7-dihydro-1H,5H-pyrazolo[1,2-a]pyrazol-1-one;
2-amino-3-ethylamino-6,7-dihydro-1H,5H-pyrazolo[1,2-a]pyrazol-1-one;
2-amino-3-isopropylamino-6,7-dihydro-1H,5H-pyrazolo[1,2-a]pyrazol-1-one;
2-amino-3-(pyrrolidin-1-yl)-6,7-dihydro-1H,5H-pyrazolo[1,2-a]pyrazol-1-one;
4,5-diamino-1,2-dimethyl-1,2-dihydropyrazol-3-one;
4,5-diamino-1,2-diethyl-1,2-dihydropyrazol-3-one;
4,5-diamino-1,2-di(2-hydroxyethyl)-1,2-dihydropyrazol-3-one;
2-amino-3-(2-hydroxyethyl)amino-6,7-dihydro-1H,5H-pyrazolo[1,2-a]pyrazol-1-one;
2-amino-3-dimethylamino-6,7-dihydro-1H,5H-pyrazolo[1,2-a]pyrazol-1-one;
2,3-diamino-5,6,7,8-tetrahydro-1H,6H-pyridazino[1,2-a]pyrazol-1-one;
4-amino-1,2-diethyl-5-pyrrolidin-1-yl-1,2-dihydropyrazol-3-one;
4-amino-5-(3-dimethylaminopyrrolidin-1-yl)-1,2-diethyl-1,2-dihydropyrazol-3-one;
2,3-diamino-6-hydroxy-6,7-dihydro-1H,5H-pyrazolo[1,2-a]pyrazol-1-one.

The at least one oxidation base of formula (I) is present in an amount ranging from 0.001% to 10% by weight, for instance ranging from 0.005% to 6% by weight relative to the total weight of the dye composition.

The at least one coupler useful in the context of the present disclosure may be chosen from meta-phenylenediamines, meta-aminophenols, meta-diphenols, naphthalene-based couplers and heterocyclic couplers, and the addition salts thereof.

Non-limiting examples that may be mentioned include, but are not limited to, 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylened ioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino)toluene, and the acid-addition salts thereof.

In the composition of the present disclosure, the at least one coupler is present in an amount ranging from 0.001% to 10% by weight, for example ranging from 0.005% to 6% by weight relative to the total weight of the dye composition.

In the context of the present disclosure, the term "polyol" means a compound comprising a saturated or unsaturated, linear, branched or cyclic hydrocarbon-based chain bearing at least two hydroxyl functions. The chain and its branches may be interrupted with 1 to 6 oxygen atoms. The chain and its branches may also bear at least one substituent other than hydroxyl groups, these substituents being chosen from carboxyl, amino, halogen and $C_6$-$C_{30}$ aryl groups.

Non-limiting examples of $C_4$-$C_{30}$ polyols that may be mentioned include, but are not limited to, branched or unbranched diols, such as 1,4-butanediol; 1,5-pentanediol; 1,6-hexanediol; neopentyl glycol (or 2,3-dimethyl-1,3-propanediol); 2,5-hexanediol; amylene glycol (or 2,4-pentanediol); hexylene glycol (or 2-methyl-2,4-pentanediol); isoprene glycol (or 3-methyl-1,3-butanediol); pinacol (or 2,3-dimethyl-2,3-butanediol); 1-methoxy-2,4-butanediol; 4-methoxy-1,2-butanediol; branched or unbranched triols, such as 1,2,4-butanetriol and 1,2,6-hexanetriol; polyethylene glycol containing 4, 6 or 7 ethylene units; dipropylene glycol.

According to at least one embodiment, the at least one polyol is $C_4$-$C_{15}$. For instance, the polyol is chosen from hexylene glycol; neopentyl glycol; and isoprene glycol.

The at least one polyol may be present in the composition in accordance with the present disclosure in an amount ranging from 0.1% to 40% by weight, for instance ranging from 0.5% to 20% by weight relative to the total weight of the composition.

The dye composition of the present disclosure may contain oxidation bases other than those of formula (I) and conventionally used for the dyeing of keratin fibers.

The composition of the present disclosure may comprise, for example, additional oxidation bases chosen from para-phenylenediamines, bis(phenyl)alkylenediamines, para-aminophenols, bis-para-aminophenols, ortho-amino-phenols, ortho-phenylenediamines and heterocyclic bases other than the compounds of formula (I) as defined above, and the addition salts thereof.

Among the para-phenylenediamines that may be used herein, for example, non-limiting mention may be made of: para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the acid-addition salts thereof.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the acid-addition salts thereof are used in at least one embodiment.

Among the bis(phenyl)alkylenediamines that may be used herein, for example, non-limiting mention may be made of: N,N-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the acid-addition salts thereof.

Among the para-aminophenols that may be used herein, for example, non-limiting mention may be made of: para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the acid-addition salts thereof.

Among the ortho-aminophenols that may be used herein, for example, non-limiting mention may be made of: 2-aminophenol, 2-amino-5-methylphenol, 2-amino-6-methylphenol and 5-acetamido-2-aminophenol, and the acid-addition salts thereof.

Among the heterocyclic bases, non-limiting mention may be made, for example, of pyridine derivatives, pyrimidine derivatives and pyrazole derivatives.

Among the pyridine derivatives, non-limiting mention may be made, of the compounds described, for example, in Patent Nos. GB 1 026 978 and GB 1 153 196, as well as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the acid-addition salts thereof.

Other pyridine oxidation bases that may be useful in the present disclosure include, but are not limited to, the 3-aminopyrazolo[1,5-a]pyridine oxidation bases or the addition salts thereof described, for example, in Patent Application No. FR 2 801 308. By way of example, non-limiting mention may be made of: pyrazolo[1,5-a]pyrid-3-ylamine; 2-acetylaminopyrazolo[1,5-a]pyrid-3-ylamine; 2-morpholin-4-ylpyrazolo[1,5-a]pyrid-3-ylamine; 3-aminopyrazolo[1,5-a]pyridine-2-carboxylic acid, 2-methoxypyrazolo[1,5-a]pyrid-3-ylamine; (3-aminopyrazolo[1,5-a]pyrid-7-yl)methanol; 2-(3-aminopyrazolo[1,5-a]pyrid-5-yl)ethanol; 2,3-aminopyrazolo[1,5-a]pyrid-7-yl)ethanol; (3-aminopyrazolo[1,5-a]pyrid-2-yl)-methanol; 3,6-diaminopyrazolo[1,5-a]pyridine; 3,4-diaminopyrazolo[1,5-a]pyridine; pyrazolo-[1,5-a]pyridine-3,7-diamine; 7-morpholin-4-ylpyrazolo[1,5-a]pyrid-3-ylamine; pyrazolo[1,5-a]pyridine-3,5-diamine; 5-morpholin-4-ylpyrazolo[1,5-a]pyrid-3-ylamine; 2-[(3-aminopyrazolo[1,5-a]pyrid-5-yl)(2-hydroxyethyl)amino]ethanol; 2-[(3-aminopyrazolo[1,5-a]pyrid-7-yl)(2-hydroxyethyl)amino]ethanol; 3-aminopyrazolo[1,5-a]pyrid-5-ol; 3-aminopyrazolo[1,5-a]pyrid-4-ol; 3-aminopyrazolo[1,5-a]pyrid-6-ol; 3-aminopyrazolo-[1,5-a]pyrid-7-ol and also the addition salts thereof with an acid or with a base.

Among the pyrimidine derivatives, non-limiting mention may be made of the compounds described, for example, in Patent No. DE 23 59 399 or Patent Nos. JP 88-169 571; JP 05 163 124; EP 0 770 375 or Patent Application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in Patent Application FR A-2 750 048 and among which non-limiting mention may be made of pyrazolo[1,5-a]-pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine and 3-amino-5-methyl-7-imidazolylpropylaminopyrazolo[1,5-a]pyrimidine, and the acid-addition salts thereof and the tautomeric forms thereof, when a tautomeric equilibrium exists.

Among the pyrazole derivatives, non-limiting mention may be made of the compounds described in Patent Nos. DE 38 43 892 and DE 41 33 957 and Patent Applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the acid-addition salts thereof.

The at least one oxidation base is present in the composition of the present disclosure in an amount for each ranging from 0.001% to 10% by weight relative to the total weight of the dye composition, such as ranging from 0.005% to 6%.

The addition salts of the at least one oxidation base and of the at least one coupler that may be used in the context of the present disclosure may be chosen from acid-addition salts, such as the hydrochlorides, hydrobromides, sulfates, citrates, succinates, tartrates, lactates, tosylates, benzenesulfonates, phosphates and acetates, and base-addition salts, such as sodium hydroxide, potassium hydroxide, ammonia, amines or alkanolamines.

The dye composition as disclosed herein may also contain at least one direct dye that may be chosen, for example, from nitrobenzene dyes, azo direct dyes and methine direct dyes. The at least one direct dye may be of nonionic, anionic or cationic nature.

The medium that is suitable for dyeing, also known as the dye support, is a cosmetic medium comprising water or a mixture of water and at least one organic solvent other than the at least one polyol useful in the context of the present disclosure. As an organic solvent, non-limiting mention may be made, for example, of $C_1$-$C_4$ lower alkanols, such as ethanol and isopropanol and aromatic alcohols such as benzyl alcohol, and mixtures thereof.

The at least one solvent other than the at least one polyol of the present disclosure is present in an amount ranging, for instance, from 1% to 40% by weight relative to the total weight of the dye composition, and further for example ranging from 5% to 30% by weight.

The dye composition as disclosed herein can also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, such as, for example, anionic, cationic, nonionic or amphoteric associative polymeric thickeners, antioxidants, penetrants, sequestrants, fragrances, buffers, dispersants, conditioning agents, for instance silicones, which may be volatile or non-volatile, and modified or unmodified, film-forming agents, ceramides, preserving agents and opacifiers.

The above adjuvants are present in the composition in an amount for each of them of ranging from 0.01% to 20% by weight relative to the weight of the dye composition.

Needless to say, a person skilled in the art will take care to select this or these optional additional compounds such that the beneficial properties intrinsically associated with the oxidation dye composition in accordance with the present disclosure are not, or are not substantially, adversely affected by the addition(s) envisaged.

The pH of the dye composition as disclosed herein ranges from 3 to 12, for instance from 5 to 11. It may be adjusted to the desired value using acidifying or basifying agents typically used in the dyeing of keratin fibers, or alternatively using standard buffer systems.

Among the acidifying agents, non-limiting mention may be made, for example, of inorganic or organic acids such as hydrochloric acid, orthophosphoric acid, sulfuric acid, carboxylic acids such as acetic acid, tartaric acid, citric acid and lactic acid, and sulfonic acids.

Among the basifying agents, non-limiting mention may be made, for example, of aqueous ammonia, alkaline carbonates, alkanolamines such as mono-, di- and triethanolamine and derivatives thereof, sodium hydroxide, potassium hydroxide and the compounds of formula (II) below:

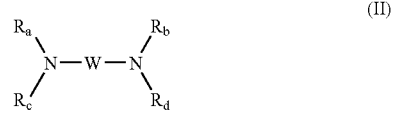

in which W is a propylene residue which is unsubstituted or substituted with a hydroxyl group or a $C_1$-$C_4$ alkyl radical; $R_a$, $R_b$, $R_c$ and $R_d$, which may be identical or different, are chosen from hydrogen atoms, $C_1$-$C_4$ alkyl radicals and $C_1$-$C_4$ hydroxyalkyl radicals.

The dye composition as disclosed herein may be in various forms, such as in the form of liquids, creams or gels, or in any other form that is suitable for dyeing keratin fibers, such as human hair.

The process of the present disclosure is a process in which the composition as disclosed herein is applied to the fibers, and the color is developed using at least one oxidizing agent. The color may be developed at acidic, neutral or alkaline pH and the oxidizing agent may be added to the composition of the present disclosure just at the time of use, or it may be used starting with an oxidizing composition containing it, which is applied simultaneously or sequentially to the composition of the present disclosure. For instance, this coloration may be developed at neutral pH.

According to at least one embodiment, the composition according to the present disclosure is mixed, for instance at the time of use, with a composition comprising, in a medium that is suitable for dyeing, at least one oxidizing agent, this oxidizing agent being present in an amount that is sufficient to develop a coloration. The mixture obtained is then applied to the keratin fibers. After an action time of 3 to 50 minutes, for example 5 to 30 minutes, the keratin fibers are rinsed, washed with shampoo, rinsed again and then dried.

The oxidizing agents conventionally used for the oxidation dyeing of keratin fibers are, for example, hydrogen peroxide, urea peroxide, alkali metal bromates, persalts such as perborates and persulfates, peracids and oxidase enzymes, among which non-limiting mention may be made of peroxidases, 2-electron oxidoreductases such as uricases, and 4-electron oxygenases, for instance laccases. For example, hydrogen peroxide is commonly used.

The oxidizing composition may also contain various adjuvants conventionally used in compositions for dyeing the hair and as defined above.

The pH of the oxidizing composition comprising the at least one oxidizing agent is such that, after mixing with the dye composition, the pH of the resulting composition applied to the keratin fibers ranges from 3 to 12, such as from 5 to 11. It may be adjusted to the desired value by means of acidifying or basifying agents usually used in the dyeing of keratin fibers and as defined above.

The ready-to-use composition that is finally applied to the keratin fibers may be in various forms, such as in the form of liquids, creams or gels or any other form that is suitable for dyeing keratin fibers, such as human hair.

Another aspect of the present disclosure is a multi-compartment dyeing device or "kit", in which a first compartment comprises the dye composition of the present disclosure defined above with the exception of the oxidizing agent and a second compartment comprises an oxidizing composition. This device may be equipped with a means for applying the desired mixture to the hair, such as the devices described in Patent FR 2 586 913.

Another aspect of the present disclosure is the use for the oxidation dyeing of keratin fibers, such as the oxidation dyeing of human keratin fibers such as the hair, using the composition as disclosed herein.

The diamino-N,N-dihydropyrazolone derivatives of formula (I) may be obtained from synthetic intermediates and synthetic routes as described in the literature, for example in the following references: J. Het. Chem., 2001, 38(3), 613-616, Helvetica Chimica Acta, 1950, 33, 1183-1194, J. Org. Chem., 23, 2029 (1958), J. Am. Chem. Soc., 73, 3240 (1951), J. Am. Chem. Soc., 84, 590 (1962), Justus Liebig Ann. Chem., 686, 134 (1965), Tetrahedron. Lett., 31, 2859-2862 (1973), U.S. Pat. Nos. 4,128,425 and 2,841,584 and the references cited therein.

According to these references, the compounds of formula (I) in which the radicals $R_3$ and $R_4$ are equal to hydrogen atoms may be obtained via the synthetic route represented by Scheme A below:

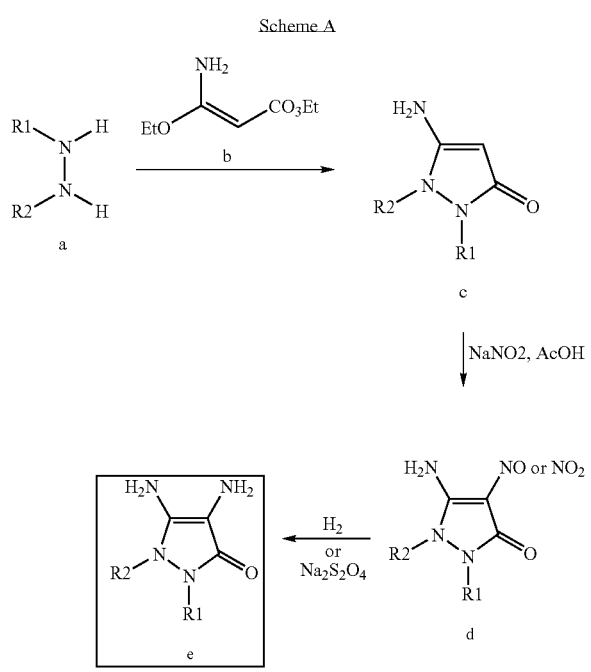

The compounds in which the radicals $R_1$ and $R_2$ simultaneously are a methyl group and the radicals $R_3$ and $R_4$ are hydrogen atoms may be obtained on the basis of the method described in Justus Lieb. Ann. Chem., 686, 134 (1965) (Scheme B):

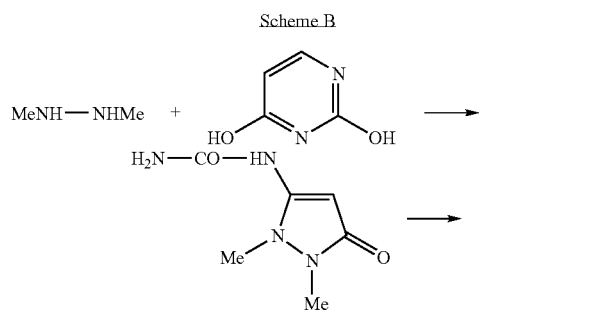

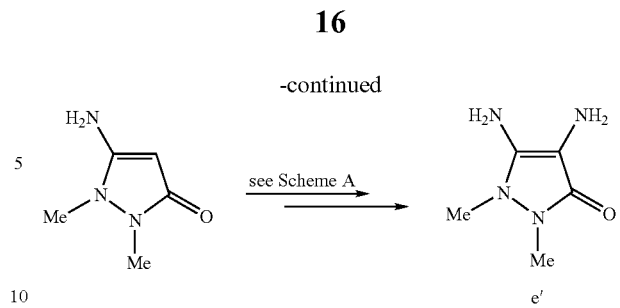

The compounds in which the radical $R_1$ is a methyl group, $R_2$ is a phenyl radical and the radicals $R_3$ and $R_4$ are hydrogen atoms may be obtained on the basis of the method described in J. Org. Chem., 23, 2029 (1958), J. Am. Chem. Soc., 73, 3240 (1951) (Scheme C):

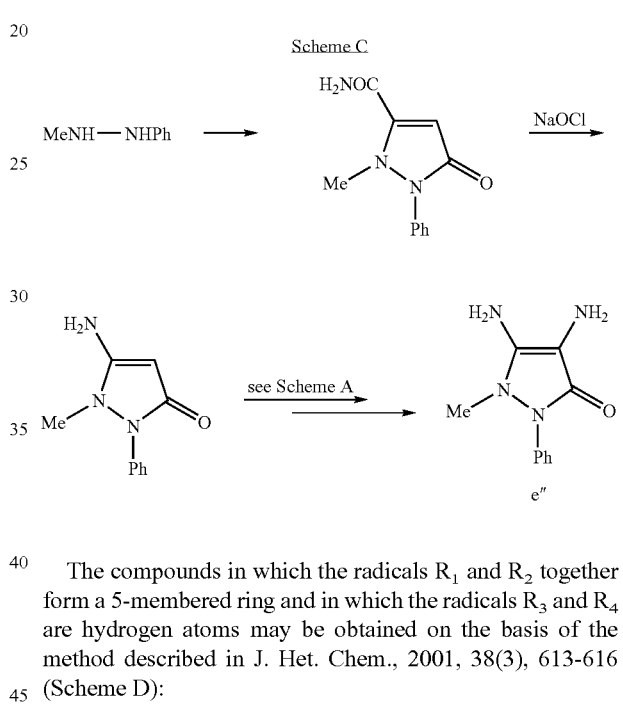

The compounds in which the radicals $R_1$ and $R_2$ together form a 5-membered ring and in which the radicals $R_3$ and $R_4$ are hydrogen atoms may be obtained on the basis of the method described in J. Het. Chem., 2001, 38(3), 613-616 (Scheme D):

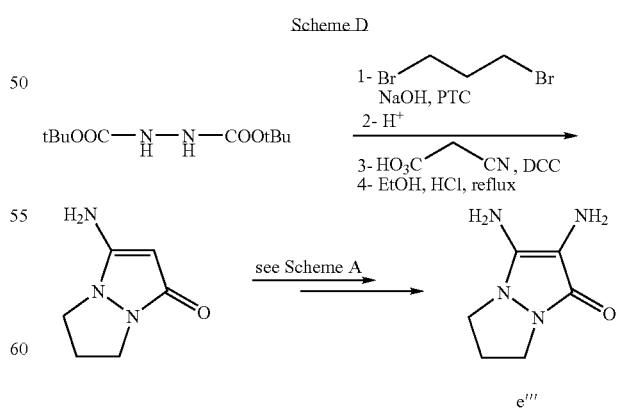

According to a different process, the compounds of formula (I) may be obtained according to the synthesis illustrated in Scheme E:

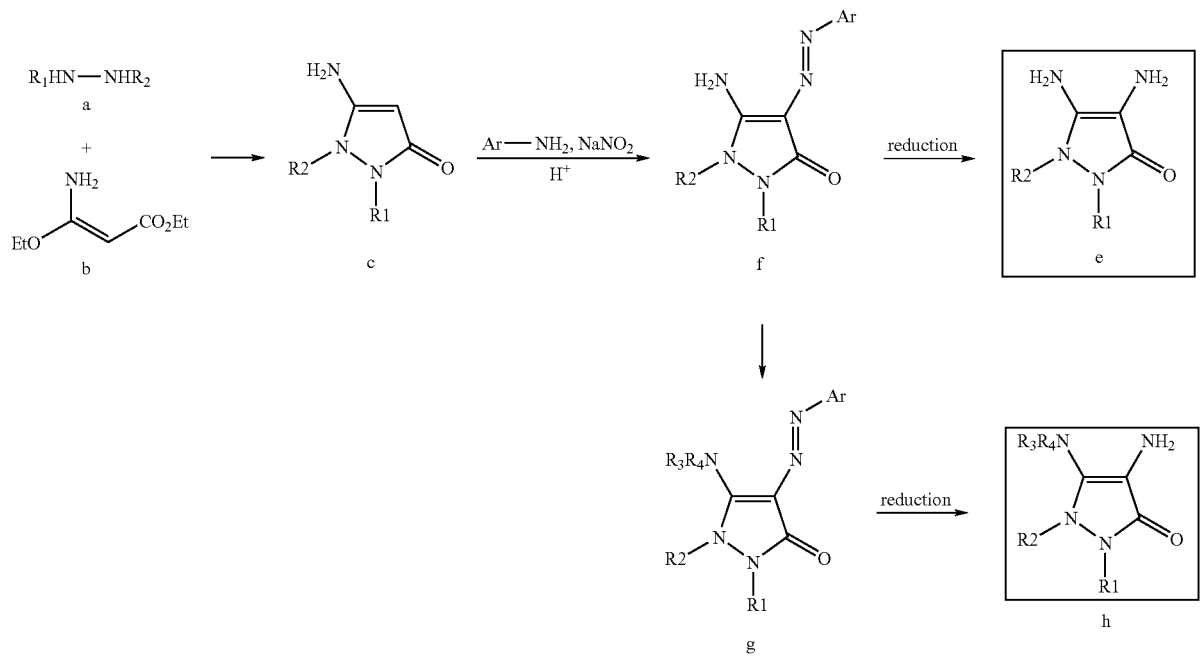

According to this process, the following steps are performed:

a) Step 1: a compound a

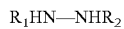

is reacted with a compound b:

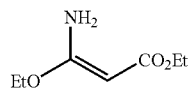

to obtain a 5-amino-1,2-dihydropyrazol-3-one compound c:

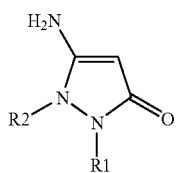

b) Step 2: the derivative c thus obtained is reacted with an aryldiazonium salt ($ArNH_2$, $NaNO_2$, $H^+$) to obtain an azo compound f:

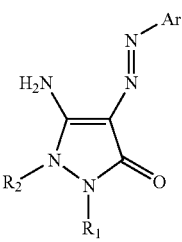

c) Step 3: a step of functionalization of the primary amine group of the resulting azo compound f is optionally performed to obtain a compound g below:

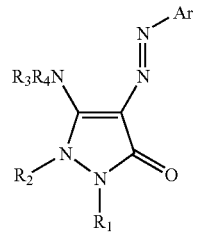

d) Step 4: a reduction reaction of the azo compound f or g is performed to obtain, respectively, an amino compound e or h:

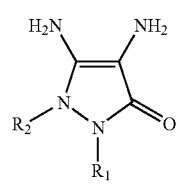

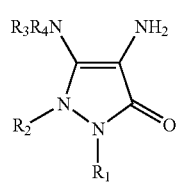

The optional step of functionalization of the primary amine group in position 5 to a secondary and tertiary amine $NR_3R_4$, to obtain the compounds g, is performed according to the standard methods of organic synthesis (alkyl halide, alkyl O-sulfonate, alkyl trialkylammonium, reductive amination, etc., see, for example, Advanced Organic Chemistry, 3rd edition, 1985, J. March, Wiley Interscience).

Reduction of the azo group leads to the compounds e and h in accordance with the present disclosure.

The reduction step is performed in a conventional manner, for example by performing a hydrogenation reaction via heterogeneous catalysis in the presence of Pd/C, Pd(II)/C, Ni/Ra, etc. or alternatively by performing a reduction reaction with a metal, for example with zinc, iron, tin, etc. (see Advanced Organic Chemistry, 3rd edition, J. March, 1985, Wiley Interscience and Reduction in Organic Chemistry, M. Hudlicky, 1983, Ellis Horwood Series Chemical Science).

According to another process, the 2,3-diamino-6,7-dihydro-1H,5H-pyrazolo[1,2-a]pyrazol-1-one and 2,3-diamino-5,6,7,8-tetrahydro-1H,6H-pyridazino[1,2-a]-pyrazol-1-one derivatives are obtained according to the synthesis illustrated by Scheme F:

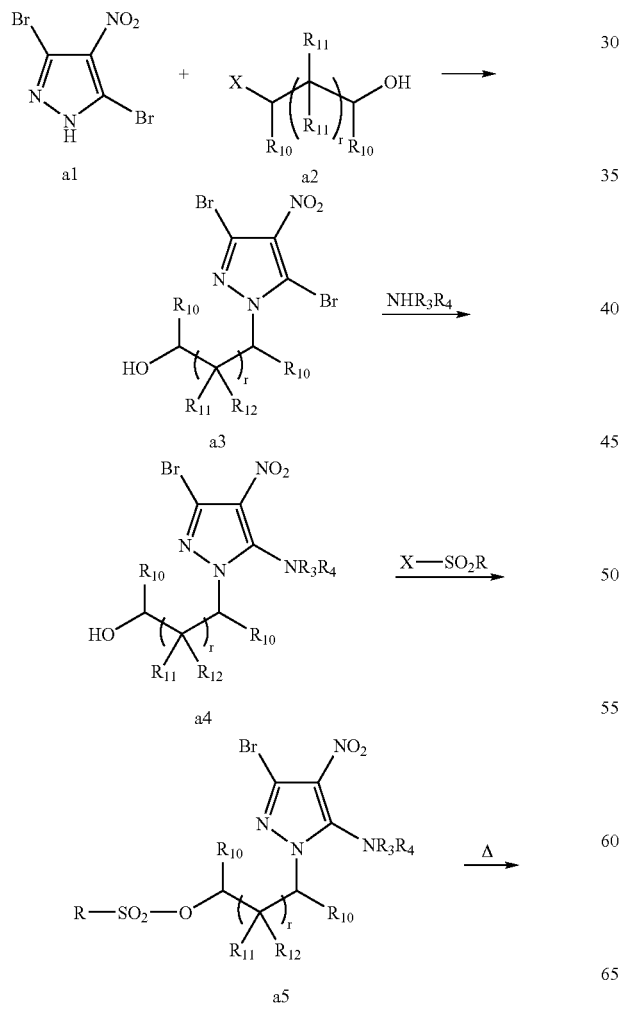

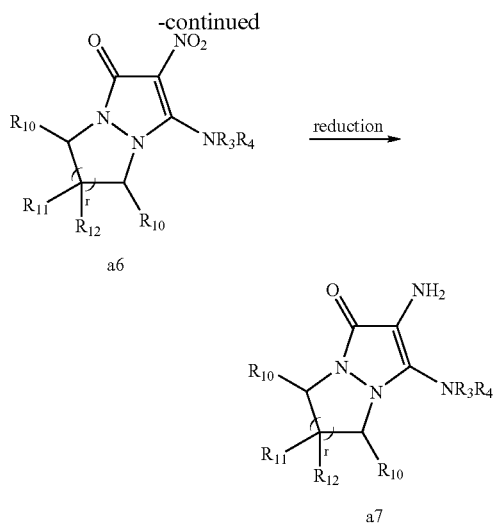

According to this process, the following steps are performed:

a) Step 1: a compound a1 below:

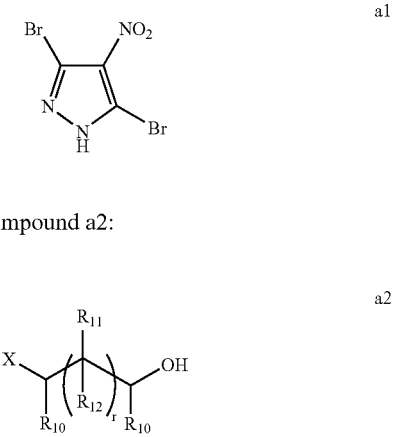

is reacted with a compound a2:

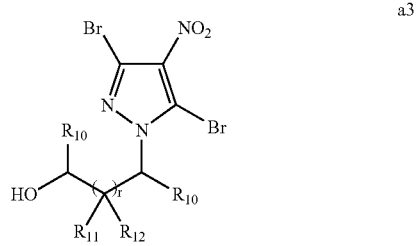

to obtain a compound a3:

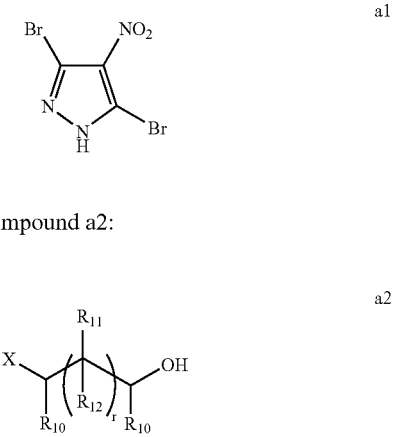

in which:
the radical $R_{10}$ is chosen from a hydrogen atom, a carboxyl; a carboxamido; a $C_1$-$C_4$ alkyl radical optionally substituted with at least one radical chosen from hydroxyl, amino, (di)alkylamino, alkoxy, carboxyl and sulfonyl radicals;
the radicals $R_{11}$ and $R_{12}$ are, independently of each other, chosen from hydrogen or halogen atoms; and from amino;

(di)($C_1$-$C_4$)alkylamino; hydroxyl; carboxyl; carboxamido; ($C_1$-$C_2$)alkoxy; and $C_1$-$C_4$ alkyl radicals optionally substituted with at least one radical chosen from hydroxyl, amino, (di)alkylamino, alkoxy, carboxyl and sulfonyl radicals;

X is chosen from a halogen atom and an alkylsulfonate radical;

r is an integer from 1 to 3.

b) Step 2: compound a3 is reacted with an amine of formula $NHR_3R_4$ to obtain a compound a4:

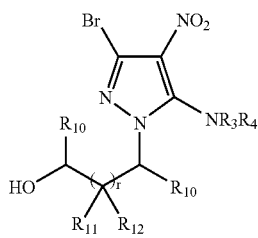

a4 c) Step 3: compound a4 is reacted with at least one alkylsulfonyl, arylsulfonyl or perfluoroalkylsulfonyl halide R—$O_2$S—$X_1$ (R is chosen from alkyl, aryl and perfluoroalkyl, $X_1$ is a halogen), in a solvent with a boiling point of between 60° C. and 190° C., to obtain a compound a5:

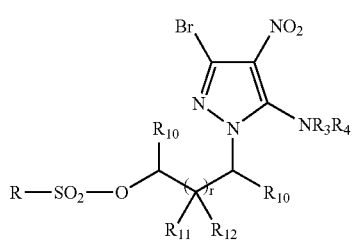

a5 d) Step 4: the resulting compound a5 is then heated in a solvent with a boiling point of between 60° C. and 190° C. to obtain a compound a6:

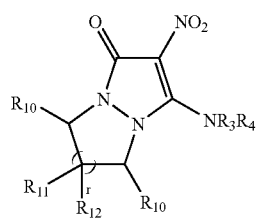

a6 e) Step 5: the compound a6 obtained is reduced to obtain the compound a7 of formula (III) below:

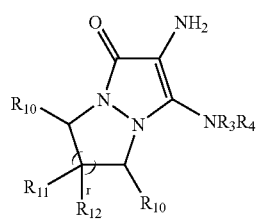

a7

Formula (III)

In at least one embodiment, according to this process, the 3,5-dibromo-4-nitropyrazole a1, obtained, for example, according to the method described in Patent No. DE 42 34 885, reacts with the reagent a2, for example in a solvent with a boiling point of from 60° C. to 190° C. Examples of solvents that may be mentioned include but are not limited to pentanol, dimethylformamide and N-methylpyrrolidine. The reaction may be performed, for example, in the presence of an organic or mineral base, for instance sodium carbonate, sodium hydroxide, sodium acetate or triethylamine. For example, the temperature of the reaction medium is maintained from 60° C. to 160° C., and further, for example, from 80° C. to 120° C.

The 1-hydroxyalkyl-3,5-dibromo-4-nitropyrazole a3 is isolated for instance by precipitation or crystallization after addition of ice to the reaction medium.

In step 2, the derivative a3 is reacted with an amine $NHR_3R_4$, for example in a solvent with a boiling point ranging from 60° C. to 190° C., for instance butanol, pentanol or dimethylformamide. For example, the temperature ranges from 60° C. to 160° C. for example from 80° C. to 120° C. After consumption of the reagents, the 5-amino-4-nitro-3-bromo-1-hydroxyalkylpyrazole compound a4 is isolated by precipitation or crystallization from water.

In accordance with step 3, the derivative a5 is obtained by reacting the alcohol a4 and an alkylsulfonyl, arylsulfonyl or perfluoroalkylsulfonyl halide. For instance, the reaction may take place in an aprotic solvent, for instance tetrahydrofuran or dioxane. The reaction may take place at a temperature ranging from –20° C. to 60° C. for example, and further ranging from 0° C. to 25° C. for example. Furthermore, this step takes place in the presence of an organic or mineral base, for instance potassium carbonate, triethylamine or N-methylmorpholine. After disappearance of the reagents, compound a5 may be isolated by precipitation or crystallization from water.

The sulfonate a5 obtained after step 3 is placed, in step 4, in solution or in dispersion in a solvent with a boiling point ranging from 60° C. to 190° C. and further ranging from 90° C. to 140° C. The temperature of the reaction medium is then brought from 90° C. to 140° C., for example from 105° C. to 125° C. until all of the sulfonate a5 has been consumed. After cooling to room temperature, the perhydropyrazolo[1,2-a]pyrazol-1-one (r=1), perhydropyridazino[1,2-a]pyrazol-1-one (r=2) or perhydrodiazepino[1,2-a]pyrazolone (r=3) compound a6 crystallizes and is isolated via the standard methods of organic synthesis.

The final compound a7 in accordance with the present disclosure is obtained, during a step 5, via reduction of the nitro derivative a6, the reduction methods used being, for example, a hydrogenation via heterogeneous catalysis in the presence of Pd/C, Pd(II)/C, Ni/Ra, etc. or alternatively such as a reduction reaction with a metal, for example with zinc, iron, tin, etc. (see Advanced Organic Chemistry, 3rd edition, J. March, 1985, Wiley Interscience and Reduction in Organic Chemistry, M. Hudlicky, 1983, Ellis Horwood Series Chemical Science).

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in its respective testing measurement.

The examples that follow are intended to illustrate the present disclosure without, however, being limiting in nature.

EXAMPLES

Example 1

Synthesis of 2,3-diamino-6,7-dihydro-1H,5H-pyrazolo[1,2-a]pyrazol-1-one dihydrochloride 5

The NMR analyses ($^1$H 400 MHz and $^{13}$C 100.61 MHz DMSO $d_6$) were performed in accordance with the expected structure.

Step 2

Synthesis of 3-[5-(benzylamino)-3-bromo-4-nitro-1H-pyrazol-1-yl]propan-1-ol 2

0.135 mol of 3-(3,5-dibromo-4-nitro-1H-pyrazol-1-yl)propan-1-ol 1 was dispersed in a 500 ml three-necked flask containing 150 ml of ethanol, the mixture was heated to 60° C. and 0.825 mol of benzylamine was then added over 30 minutes.

After 6 hours at 60° C., the reaction medium was cooled to room temperature.

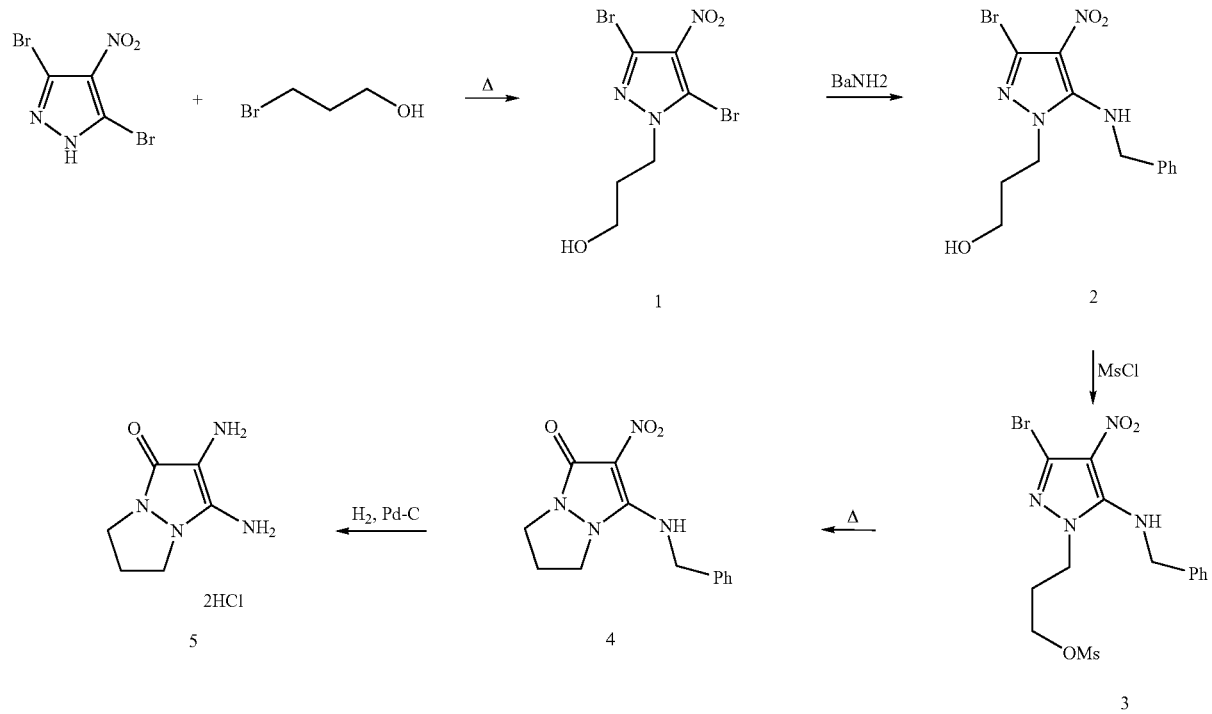

Step 1

Synthesis of 3-(3,5-dibromo-4-nitro-1H-pyrazol-1-yl)propan-1-ol 1

0.369 mol of sodium acetate was introduced into a solution of 0.184 mol of dibromonitropyrazole in 250 ml of N-methylpyrrolidone in a 500 ml three-necked flask, and the reaction medium was brought to 80° C.

0.369 mol of 3-bromopropanol was added dropwise at this temperature. This temperature was maintained for 5 hours.

After cooling to room temperature, the medium was poured onto ice with stirring.

The 3-(3,5-dibromo-4-nitro-1H-pyrazol-1-yl)propan-1-ol 1 precipitates. It was filtered off by suction, dried and obtained in a yield of 75%.

The mass of the expected compound $C_6H_7Br_2N_3O_3$ was detected by mass spectrometry.

The 3-[5-(benzylamino)-3-bromo-4-nitro-1H-pyrazol-1-yl]propan-1-ol 2 was precipitated by pouring the reaction medium onto 1 litre of ice with stirring. After filtration by suction and drying under vacuum in the presence of $P_2O_5$, compound 2 was isolated in a yield of 90%.

The NMR analyses ($^1$H 400 MHz and $^{13}$C 100.61 MHz DMSO $d_6$) were in accordance with the expected structure.

Elemental Analysis:

| Theory: | C43.96 | H4.26 | N15.77 | O13.51 | Br22.50 |
|---|---|---|---|---|---|
| Found: | C44.09 | H4.22 | N15.44 | O14.37 | Br21.50 |

Step 3

Synthesis of 3-[5-(benzylamino)-3-bromo-4-nitro-1H-pyrazol-1-yl]propyl methanesulfonate 3

0.126 mol of 3-[5-(benzylamino)-3-bromo-4-nitro-1H-pyrazol-1-yl]propan-1-ol 2 and 15.82 mol of triethylamine were introduced, with stirring, into a 500 ml three-necked flask containing 200 ml of THF. The mixture obtained was then cooled to 5° C. and 0.126 mol of mesyl chloride was poured in over 45 minutes.

The reaction medium was maintained at this temperature for 2 hours and the 3-[5-(benzylamino)-3-bromo-4-nitro-1H-pyrazol-1-yl]propyl methanesulfonate 3 was then precipitated by pouring the reaction medium onto 800 ml of ice.

After filtering, the solid was washed thoroughly with water and with diisopropyl ether. Drying was performed under vacuum in the presence of $P_2O_5$. The yield for this step was 94%.

The mass of the expected compound $C_{14}H_{17}BrN_4O_5S$ was detected by mass spectrometry.

The NMR analyses ($^1$H 400 MHz and $^{13}$C 100.61 MHz DMSO $d_6$) were in accordance with the expected structure.

Elemental Analysis:

| Theory: | C38.81 | H3.96 | N12.93 | O18.46 | S7.40 | Br18.44 |
|---|---|---|---|---|---|---|
| Found: | C39.03 | H3.91 | N12.83 | O18.52 | S7.29 | Br18.26 |

Step 4

Synthesis of 3-(benzylamino)-2-nitro-6,7-dihydro-1H,5H-pyrazolo[1,2-a]pyrazol-1-one 4

0.1 mol of 3-[5-(benzylamino)-3-bromo-4-nitro-1H-pyrazol-1-yl]propyl methanesulfonate 3 was dispersed in a 500 ml three-necked flask containing 300 ml of pentanol, and the reaction medium was maintained at 130° C. for 2 hours.

After cooling to room temperature, the solid formed was filtered off by suction on a sinter funnel, washed with diisopropyl ether and dried under vacuum in the presence of $P_2O_5$. The 3-(benzylamino)-2-nitro-6,7-dihydro-1H,5H-pyrazolo[1,2-a]pyrazol-1-one 4 was obtained in a yield of 86%.

The NMR analyses ($^1$H 400 MHz and $^{13}$C 100.61 MHz DMSO $d_6$) were in accordance with the expected structure.

The mass of the expected compound $C_6H_{11}N_4O$ was detected by mass spectrometry.

Elemental Analysis:

| Theory: | C56.72 | H5.49 | N20.36 | O17.44 |
|---|---|---|---|---|
| Found: | C56.68 | H5.13 | N20.38 | O17.69 |

Step 5

Synthesis of 2,3-diamino-6,7-dihydro-1H,5H-pyrazolo[2-a]pyrazol-1-one dihydrochloride 5

20 g of 3-(benzylamino)-2-nitro-6,7-dihydro-1H,5H-pyrazolo[1,2-a]pyrazol-1-one 4 and 4 g of 5% palladium-on-charcoal were introduced into a 1 litre autoclave containing 800 ml of ethanol. The reduction was then performed under a hydrogen pressure of 8 bar and at a temperature of from 50° C. to 100° C. (stirring at 1000 to 2500 rpm).

After reaction for 4 hours, there was no further consumption of hydrogen and the medium was cooled to 20° C.

The catalyst was removed under nitrogen by filtration, and hydrochloric ethanol was then added to the filtrate. The crystalline product was filtered off by suction, washed with diisopropyl ether and then dried under vacuum in the presence of $P_2O_5$. The 2,3-diamino-6,7-dihydro-1H,5H-pyrazolo[1,2-a]pyrazol-1-one dihydrochloride 5 was obtained in a yield of 89%.

The mass of the expected compound was detected by mass spectrometry.

The NMR analyses ($^1$H 400 MHz and $^{13}$C 100.61 MHz DMSO $d_6$) were in accordance with the expected structure.

Elemental Analysis:

| Theory: | C31.73 | H5.33 | N24.67 | O7.07 | C131.22 |
|---|---|---|---|---|---|
| Found: | C31.45 | H5.20 | N24.62 | O7.24 | C130.86 |

Example 2

Synthesis of 2-amino-3-(ethylamino)-6,7-dihydro-1H,5H-pyrazolo[1,2-a]pyrazol-1-one dihydrochloride 9

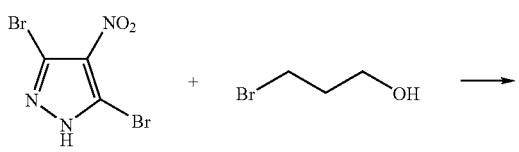

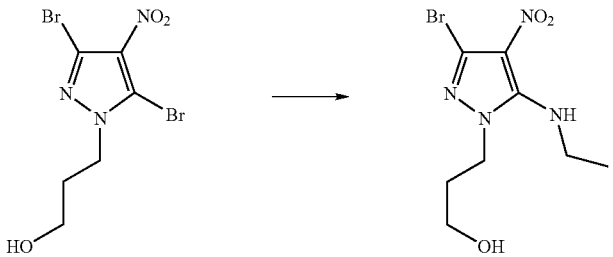

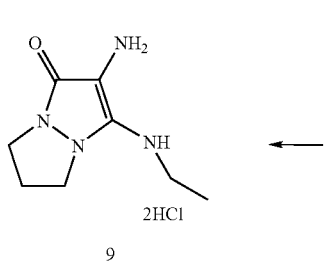 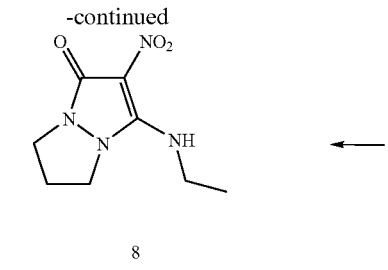 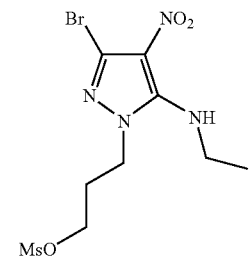

Step 2

Synthesis of 3-[3-bromo-5-(ethylamino)-4-nitro-1H-pyrazol-1-yl]propan-1-ol 6

15 mmol of 3-(3,5-dibromo-4-nitro-1H-pyrazol-1-yl)propan-1-ol was introduced into 30 ml of ethanol in a three-necked flask, with stirring. The homogeneous medium was heated to 75° C. and 93 mmol of ethylamine was then added dropwise and stirring was continued for four hours.

After cooling to room temperature, the medium was poured onto ice and the 3-[3-bromo-5-(ethylamino)-4-nitro-1H-pyrazol-1-yl]propan-1-ol 6 precipitates.

The yellow solid was filtered off by suction and then washed thoroughly with water and diisopropyl ether. Drying was performed under vacuum in the presence of $P_2O_5$. The recovered mass was 3.6 g.

The NMR analyses ($^1$H 400 MHz and $^{13}$C 100.61 MHz DMSO $d_6$) were in accordance with the expected structure.

The mass of the expected compound $C_8H_{13}BrN_4O_3$ was detected by mass spectrometry.

Step 3

Synthesis of 3-[5-(ethylamino)-3-bromo-4-nitro-1H-pyrazol-1-yl]propyl methanesulfonate 7

11.2 mmol of 3-[3-bromo-5-(ethylamino)-4-nitro-1H-pyrazol-1-yl]propan-1-ol 6 and 1.6 ml of triethylamine were introduced, with stirring, into a 100 ml three-necked flask containing 30 ml of THF. The homogeneous orange mixture obtained was cooled to 0° C. and 1.44 ml of mesyl chloride are added over 20 minutes.

The reaction medium was maintained at this temperature for 2 hours and the 3-[5-(ethylamino)-3-bromo-4-nitro-1H-pyrazol-1-yl]propyl methanesulfonate 7 was precipitated by pouring the reaction medium onto 500 ml of ice.

The yellow solid was filtered by suction and then washed thoroughly with water and diisopropyl ether; drying was performed under vacuum in the presence of $P_2O_5$. The recovered mass was 3.1 g.

The NMR analyses ($^1$H 400 MHz and $^{13}$C 100.61 MHz DMSO $d_6$) were in accordance with the expected structure.

The mass of the expected compound $C_9H_{15}BrN_4O_5S$ was detected by mass spectrometry.

Step 4

Synthesis of 3-(ethylamino)-2-nitro-6,7-dihydro-1H,5H-pyrazolo[1,2-a]pyrazol-1-one 8

8 mmol of 3-[5-(ethylamino)-3-bromo-4-nitro-1H-pyrazol-1-yl]propyl methanesulfonate 7 was dispersed, with stirring, in a 50 ml three-necked flask containing 20 ml of pentanol, and the reaction medium was maintained at 130° C. for 2 hours.

After cooling to room temperature, the solid formed was filtered off by suction and then washed with diisopropyl ether.

After drying under vacuum in the presence of $P_2O_5$, 1.46 g of 3-(ethylamino)-2-nitro-6,7-dihydro-1H,5H-pyrazolo[1,2-a]pyrazol-1-one 8 were obtained.

The NMR analyses ($^1$H 400 MHz and $^{13}$C 100.61 MHz DMSO $d_6$) were in accordance with the expected structure.

The mass of the expected compound was detected by mass spectrometry.

Step 5

Synthesis of 2-amino-3-(ethylamino)-6,7-dihydro-1H,5H-pyrazolo[1,2-a]pyrazol-1-one dihydrochloride 9

1.45 g of 3-(ethylamino)-2-nitro-6,7-dihydro-1H,5H-pyrazolo[1,2-a]pyrazol-1-one 8 and 300 mg of 5% palladium-on-charcoal were introduced into a 300 ml autoclave containing 200 ml of ethanol. The reduction was performed at a hydrogen pressure of 8 bar at a temperature of 60° C. (stirring at 1700 rpm).

After reaction for 2 hours, there was no further consumption of hydrogen and the reaction medium was cooled to 20° C.

The catalyst was removed by filtration under nitrogen and the filtrate was diluted with 100 ml of hydrochloric isopropyl ether.

The pale yellow solution was evaporated to dryness and the solid was then taken up in an ethanol/isopropyl ether mixture. The 2-amino-3-(ethylamino)-6,7-dihydro-1H,5H-pyrazolo[1,2-a]pyrazol-1-one hydrochloride 9 precipitated; it was filtered off by suction and, after drying under vacuum in the presence of $P_2O_5$, 1.18 g of 2-amino-3-(ethylamino)-6,7-dihydro-1H,5H-pyrazolo[1,2-a]pyrazol-1-one dihydrochloride 9 was recovered.

The NMR analyses ($^1$H 400 MHz and $^{13}$C 100.61 MHz DMSO $d_6$) were in accordance with the expected structure.

The mass of the expected compound $C_8H_{14}N_4O$ was detected by mass spectrometry.

Example 3

Synthesis of 2-amino-3-(isopropylamino)-6,7-dihydro-1H,5H-pyrazolo[1,2-a]pyrazol-1-one 13

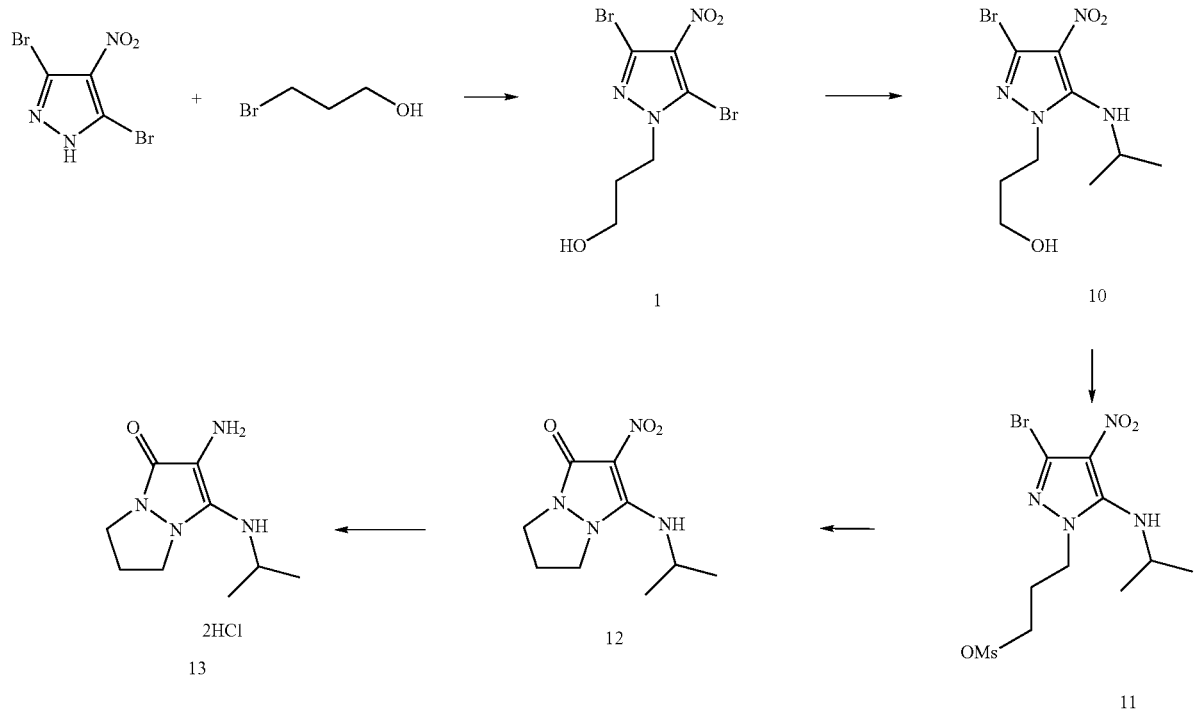

Step 2

Synthesis of 3-[3-bromo-5-(isopropylamino)-4-nitro-1H-pyrazol-1-yl]propan-1-ol 10

15 mmol of 3-(3,5-dibromo-4-nitro-1H-pyrazol-1-yl)propan-1-ol was introduced, with stirring, into 30 ml of ethanol in a three-necked flask. The homogeneous medium was heated to 75° C. and 93 mmol of isopropylamine were then added dropwise with continued stirring for 4 hours.

After cooling to room temperature, the medium was poured onto ice and then neutralized with hydrochloric acid. The 3-[3-bromo-5-(isopropylamino)-4-nitro-1H-pyrazol-1-yl]propan-1-ol 10 was extracted with dichloromethane.

After drying the organic phase over sodium sulfate and removing the solvent by evaporation under vacuum, 4.37 g of 3-[3-bromo-5-(isopropylamino)-4-nitro-1H-pyrazol-1-yl] propan-1-ol 10 was obtained.

The NMR analyses ($^1$H 400 MHz and $^{13}$C 100.61 MHz DMSO $d_6$) were in accordance with the expected structure.

The mass of the expected compound $C_9H_{15}BrN_4O_3$ was detected by mass spectrometry.

Step 3

Synthesis of 3-[5-(isopropylamino)-3-bromo-4-nitro-1H-pyrazol-1-yl]propyl methanesulfonate 11

13.7 mmol of 3-[3-bromo-5-(isopropylamino)-4-nitro-1H-pyrazol-1-yl]propan-1-ol 10 and 1.94 ml of triethylamine were introduced, with stirring, into a 50 ml three-necked flask containing 20 ml of THF. The homogeneous orange mixture thus obtained was cooled to 0° C. and 1.76 ml of mesyl chloride was added over 20 minutes.

The reaction medium was maintained at this temperature for 2 hours, and 3-[5-(ethylamino)-3-bromo-4-nitro-1H-pyrazol-1-yl]propyl methanesulfonate 11 was then precipitated by pouring the reaction medium onto 500 ml of ice.

The yellow solid was filtered off by suction and then washed thoroughly with water and petroleum ether, and was dried under vacuum in the presence of $P_2O_5$. The recovered mass was 4.2 g.

The NMR analyses ($^1$H 400 MHz and $^{13}$C 100.61 MHz DMSO $d_6$) were in accordance with the expected structure.

The mass of the expected compound was detected by mass spectrometry.

Step 4

Synthesis of 3-(isopropylamino)-2-nitro-6,7-dihydro-1H,5H-pyrazolo1,2-a]pyrazol-1-one 12

10 mmol of 3-[5-(isopropylamino)-3-bromo-4-nitro-1H-pyrazol-1-yl]propyl methanesulfonate 11 was dispersed, with stirring, in 20 ml of pentanol in a 50 ml three-necked flask, and the mixture was heated at 130° C. for 2 hours.

After cooling to room temperature, the solid obtained was filtered off by suction on a sinter funnel and washed with diisopropyl ether.

After drying under vacuum in the presence of $P_2O_5$, 1.71 g of 3-(isopropylamino)-2-nitro-6,7-dihydro-1H,5H-pyrazolo[1,2-a]pyrazol-1-one 12 was obtained.

The NMR analyses ($^1$H 400 MHz and $^{13}$C 100.61 MHz DMSO $d_6$) were in accordance with the expected structure.

The mass of the expected compound $C_9H_{14}N_4O_3$ was detected by mass spectrometry.

Step 5

Synthesis of 2-amino-3-(isopropylamino)-6,7-dihydro-1H,5H-pyrazolo[1,2-a]pyrazol-1-one dihydrochloride 13

1.70 g of 3-(isopropylaminoamino)-2-nitro-6,7-dihydro-1H,5H-pyrazolo[1,2-a]pyrazol-1-one 12 and 300 mg of 5% palladium-on-charcoal were introduced into a 300 ml autoclave containing 200 ml of ethanol. The reaction was performed at a temperature of 60° C. and at a hydrogen pressure of 6 bar (stirring at 2000 rpm).

After reaction for 2 hours, there was no further consumption of hydrogen, and the medium was cooled to 20° C.

The catalyst was removed by filtration under nitrogen after cooling to room temperature, and hydrochloric isopropyl ether was added.

The pale yellow solution was evaporated to dryness and the solid was then taken up in 50 ml of diisopropyl ether saturated with hydrogen chloride, and the precipitate was recovered by suction filtration. After drying under vacuum in the presence of $P_2O_5$, 1.5 g of 2-amino-3-(isopropylamino)-6,7-dihydro-1H,5H-pyrazolo[1,2-a]pyrazol-1-one dihydrochloride 13 was isolated.

The NMR analyses ($^1H$ 400 MHz and $^{13}C$ 100.61 MHz DMSO $d_6$) were in accordance with the expected structure.

The mass of the expected compound $C_9H_{16}N_4O$ was detected by mass spectrometry.

Example 4

2-Amino-3-(pyrrolidin-1-yl)-6,7-dihydro-1H,5H-pyrazolo[1,2-a]pyrazol-1-one dihydrochloride 17

Step 2

3-(3-Bromo-4-nitro-5-(pyrrolidin-1-yl)-1H-pyrazol-1-yl)propan-1-ol 14

15 mmol of 3-(3,5-dibromo4-nitro-1H-pyrazol-1-yl)propan-1-ol was introduced, with stirring, into 20 ml of isopropanol in a three-necked flask. The homogeneous medium was heated to 75° C. and 90 mmol of pyrrolidine was then added dropwise and stirring was continued for 2 hours.

After cooling to room temperature, the medium was poured onto ice and neutralized with hydrochloric acid. The 3-(3-bromo-4-nitro-5-(pyrrolidin-1-yl)-1H-pyrazol-1-yl)propan-1-ol 14 was extracted with dichloromethane.

After drying the organic phase over sodium sulfate and distilling off the solvent by evaporation under vacuum, 4.8 g of 3-(3-bromo-4-nitro-5-(pyrrolidin-1-yl)-1H-pyrazol-1-yl)propan-1-ol 14 was obtained.

The NMR analyses ($^1H$ 400 MHz and $^{13}C$ 100.61 MHz DMSO $d_6$) were in accordance with the expected structure.

The mass of the expected compound $C_{10}H_{17}BrN_4O$ was detected by mass spectrometry.

Step 3

Synthesis of 3-(3-bromo4-nitro-5-(pyrrolidin-1-yl)-1H-pyrazol-1-yl)propyl methanesulfonate 15

30 mmol of 3-(3-bromo-4-nitro-5-(pyrrolidin-1-yl)-1H-pyrazol-1-yl)propan-1-ol 14 and 4.25 ml of triethylamine were introduced, with stirring, into a 100 ml three-necked flask containing 50 ml of THF. The homogeneous orange mixture obtained was cooled to 0° C. and 2.32 ml of mesyl chloride was added over 20 minutes.

The reaction medium was maintained at this temperature for 2 hours and the 3-(3-bromo-4-nitro-5-(pyrrolidin-1-yl)-1H-pyrazol-1-yl)propyl methanesulfonate 15 was then precipitated by pouring the reaction medium onto ice.

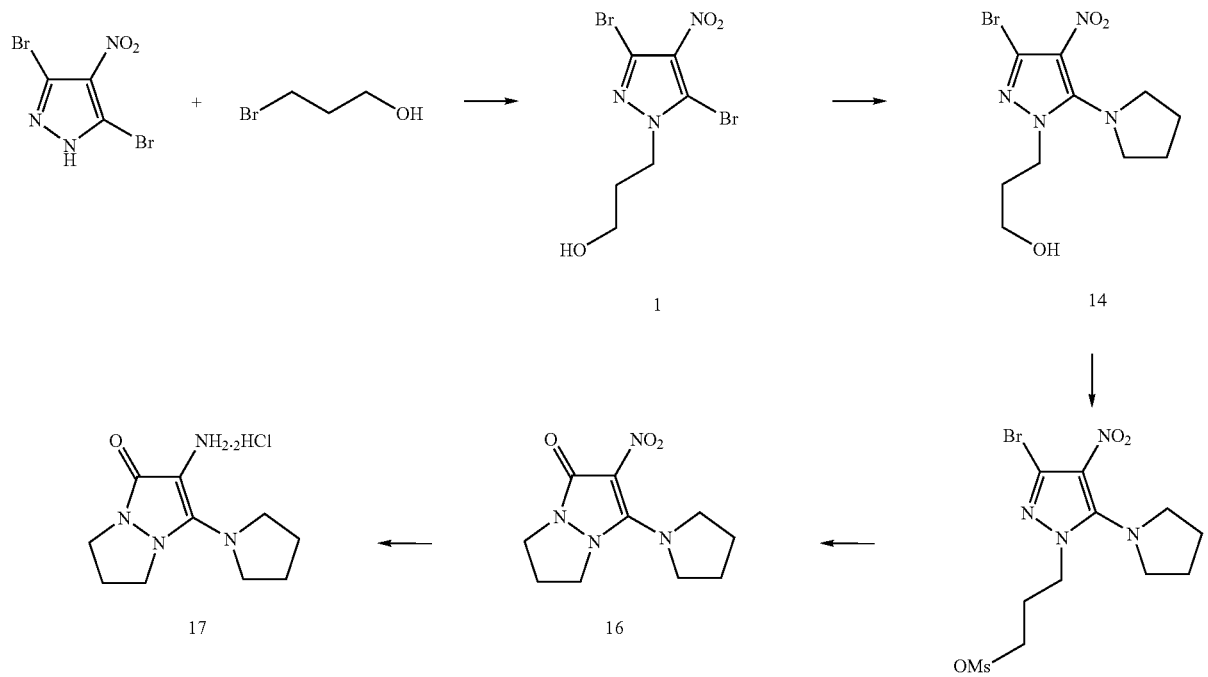

The solid was filtered off by suction and then dried under vacuum in the presence of $P_2O_5$. The recovered mass was 9.3 g.

The NMR analyses ($^1$H 400 MHz and $^{13}$C 100.61 MHz DMSO $d_6$) were in accordance with the expected structure.

The mass of the expected compound $C_{11}H_{19}BrN_4O_3S$ was detected by mass spectrometry.

Step 4

Synthesis of 2-nitro-3-(pyrrolidin-1-yl)-6,7-dihydro-1H,5H-pyrazolo[1,2-a]pyrazol-1-one 16

22.5 mmol of 3-(3-bromo-4-nitro-5-(pyrrolidin-1-yl)-1H-pyrazol-1-yl)propyl methanesulfonate 15 was introduced into 100 ml of pentanol, with stirring, in a 250 ml three-necked flask. The medium thus obtained was maintained at 130° C. for 2 hours.

After cooling to room temperature, the 2-nitro-3-(pyrrolidin-1-yl)-6,7-dihydro-1H,5H-pyrazolo[1,2-a]pyrazol-1-one 16 was extracted with dichloromethane.

After drying the organic phase over sodium sulfate and distilling off the solvent under vacuum, 1.2 g of 2-nitro-3-pyrrolidin-1-yl-6,7-dihydro-1H,5H-pyrazolo[1,2-a]pyrazol-1-one 16 was obtained.

The NMR analyses ($^1$H 400 MHz and $^{13}$C 100.61 MHz DMSO $d_6$) were in accordance with the expected structure.

The mass of the expected compound $C_{10}H_{14}N_4O_3$ was detected by mass spectrometry.

Step 5

Synthesis of 2-amino-3-(pyrrolidin-1-yl)-6,7-dihydro-1H,5H-pyrazolo[1,2-a]pyrazol-1-one dihydrochloride 17

1.1 g of 2-nitro-3-(pyrrolidin-1-yl)-6,7-dihydro-1H,5H-pyrazolo[1,2-a]pyrazol-1-one 16 and 300 mg of 5% palladium-on-charcoal were introduced into a 300 ml autoclave containing 200 ml of ethanol. The reduction was performed with stirring at 2000 rpm, at a temperature of 60° C. And under a hydrogen pressure of 6 bar.

After reaction for 2 hours, there was no further consumption of hydrogen, and the medium was cooled to 20° C.

The catalyst was removed by filtration under nitrogen after cooling to room temperature, and hydrochloric isopropyl ether was added.

The pale yellow solution was evaporated to dryness and the solid was then taken up in 50 ml of diisopropyl ether saturated with hydrogen chloride, and the precipitate was recovered by suction filtration. After drying under vacuum in the presence of $P_2O_5$, 1.5 g of 2-amino-3-(pyrrolidin-1-yl)-6,7-dihydro-1H,5H-pyrazolo[1,2-a]pyrazol-1-one dihydrochloride 17 was obtained.

The NMR analyses ($^1$H 400 MHz and $^{13}$C 100.61 MHz DMSO $d_6$) were in accordance with the expected structure.

The mass of the expected compound $C_{10}H_{16}N_4O$ was detected by mass spectrometry.

Example 5

Synthesis of 2,3-diamino-6,7-dihydro-1H,5H-pyrazolo[1,2-a]pyrazol-1-one dimethanesulfonate

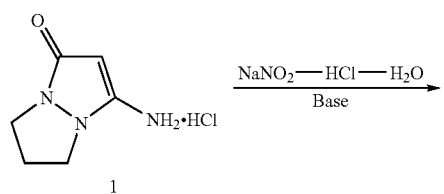

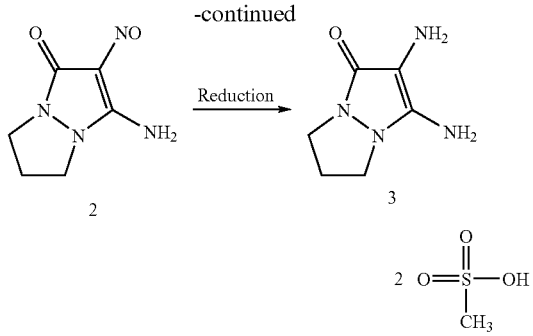

Synthesis of 3-amino-2-nitroso-6,7-dihydro-1H,5H-pyrazolo[1,2-a]pyrazol-1-one: 2

43 g (0.245 mol) of 3-amino-6,7-dihydro-1H,5H-pyrazolo[1,2-a]pyrazol-1-one hydrochloride were dissolved, with stirring, at room temperature, in a mixture of 180 ml of water and 35 ml of 35% hydrochloric acid in a 500 ml three-necked flask.

The mixture was cooled to 0° C. and a solution of 17.3 g of sodium nitrite (0.25 mol) in 20 ml of water was added dropwise over 30 minutes. The temperature of the reaction medium was maintained from 0 to 5° C. throughout the addition and for one hour after the end of the addition.

The reaction medium was brought to pH 8 by adding sodium hydroxide, with stirring, while maintaining the temperature from 0 and 5° C. The 3-amino-2-nitroso-6,7-dihydro-1H,5H-pyrazolo[1,2-a]pyrazol-1-one 2 precipitated in the form of a red-orange solid, which was filtered off on a No. 4 sinter funnel, slurried in a minimum amount of 2-propanol, washed with diisopropyl ether and dried under vacuum in the presence of phosphorus pentoxide. 35 g of orange-red product was thus obtained (yield: 85%).

The NMR ($^1$H 400 MHz and $^{13}$C 100.61 MHz DMSO $d_6$) and mass spectra were in accordance with the expected structure 2.

Synthesis of 2,3-diamino-6,7-dihydro-1H,5H-pyrazolo[1,2-a]pyrazol-1-one dimethanesulfonate: 3

33.6 g (0.2 mol) of 3-amino-2-nitroso-6,7-dihydro-1H,5H-pyrazolo[1,2-a]pyrazol-1-one 2, 500 ml of ethanol and 6 g of 5% palladium-on-charcoal containing 50% water were introduced into a 1 litre autoclave.

The medium was flushed 3 times with nitrogen and then 3 times with hydrogen and the temperature of the mixture was brought to 40° C.

The reduction was performed over two hours at a pressure of 8 bar. This reduction was exothermic and the temperature spontaneously rose to 70° C.

The temperature was allowed to fall to 50° C. and the catalyst was then filtered off on a filterpress under a stream of nitrogen.

The filtrate was poured into a mixture of 50 ml of ethanol and 40 ml of methanesulfonic acid, with cooling to 0° C. The 2,3-diamino-6,7-dihydro-1H,5H-pyrazolo-[1,2-a]pyrazol-1-one dimethanesulfonate 3 crystallized in the form of a pale yellow solid, which was filtered off by suction on a No. 4 sinter funnel, washed with diisopropyl ether and then with petroleum ether and finally dried under vacuum in the presence of phosphorus pentoxide. 43 g of pale yellow solid was thus obtained (yield: 65%).

The NMR ($^1$H 400 MHz and $^{13}$C 100.61 MHz DMSO $d_6$) and mass spectra were in accordance with the expected structure 3.

Elemental Analysis:

| Theory: | C27.74 | H5.23 | N16.17 | O32.33 | S18.51 |
|---|---|---|---|---|---|
| Found: | C27.16 | H5.22 | N15.63 | O32.81 | S18.64 |

Example 6

Synthesis of 2,3-diamino-5,6,7,8-tetrahydro-1H-pyrazolo[1,2-a]pyridazin-1-one hydrochloride

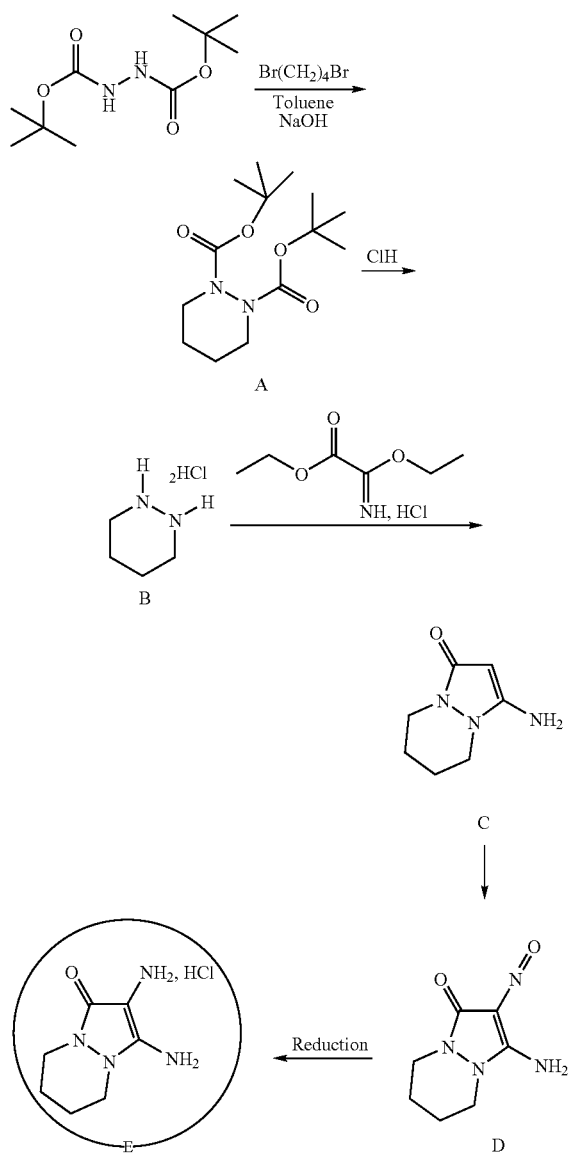

Synthesis of di-tert-butyl tetrahydropyridazine-1,2-dicarboxylate: A 50 ml of toluene, 5 g (21.5 mmol) of N,N'-di-tert-butoxycarbonyl hydrazide, 680 mg of tetraethylammonium bromide and 25 ml of 50% sodium hydroxide were introduced, with mechanical stirring, into a 250 ml three-necked flask equipped with a condenser, a thermometer and a dropping funnel.

The heterogeneous medium was heated to 100° C. and 1,4-dibromobutane was then added dropwise over 15 minutes.

The reaction medium was heated at 100° C. for 3 days. After cooling, 100 ml of ethyl acetate was added and the mixture was transferred into a separating funnel. The organic phase was washed with 4 times 70 ml of saturated aqueous sodium carbonate solution and then with 4×70 ml of water and finally with 4×70 ml of brine. The organic phase was dried over sodium sulfate and the solvent was evaporated off under vacuum. A colorless oil that crystallized as a white solid was thus obtained.

A mass of 6.1 g was recovered (yield: 99%).

The NMR ($^1$H 400 MHz and $^{13}$C 100.61 MHz DMSO $d_6$) and mass spectra were performed in accordance with the expected structure A.

Synthesis of Hexahydropyridazine Dihydrochloride: B 5.9 g of compound A was introduced into 50 ml of a 3/1 mixture of dioxane and 35% hydrochloric acid, with mechanical stirring, in a 100 ml three-necked flask equipped with a condenser and a thermometer.

The colorless solution obtained was stirred at room temperature for 3 hours and the reaction medium was then diluted with diisopropyl ether. The solvents were evaporated off under vacuum. The pasty residue obtained was taken up in an ether/ethanol mixture. After filtering off the solid and drying under vacuum, 1.39 g of white solid was obtained.

The NMR ($^1$H 400 MHz and $^{13}$C 100.61 MHz DMSO $d_6$) and mass spectra were in accordance with the expected structure B.

Synthesis of 3-amino-5,6,7,8-tetrahydro-1H-pyrazolo[1,2-a]pyridazin-1-one: C 7.5 ml of ethanol, 1.5 ml of triethylamine and 0.73 ml of 3-amino-3-ethoxyacrylic acid were introduced, with mechanical stirring, into a 25 ml three-necked flask equipped with a condenser and a thermometer. 500 mg of hexahydropyridazine dihydrochloride (compound B) were then added and the mixture was stirred for 3 hours at room temperature.

The insoluble material was filtered off and the solvent was distilled off under vacuum. The solid was taken up in a minimum amount of water, filtered off and dried under vacuum. 0.9 g of a slightly yellow powder was thus obtained.

The NMR ($^1$H 400 MHz and $^{13}$C 100.61 MHz DMSO $d_6$) and mass spectra were in accordance with the expected structure C.

Synthesis of 3-amino-2-nitroso-5,6,7,8-tetrahydro-1H-pyrazolo[1,2-a]pyridazin-1-one: D 20 ml of 35% hydrochloric acid and 1 g of 3-amino-5,6,7, 8-tetrahydro-1H-pyrazolo[1,2-a]pyridazin-1-one (compound C) were introduced, with mechanical stirring, into a 50 ml three-necked flask equipped with a condenser and a thermometer.

The mixture was cooled to 0° C. and a solution of 675 mg of sodium nitrite in 5 ml of water was added, while maintaining this temperature. The color of the reaction mixture changed from yellow to orange and a precipitate began to form.

After 30 minutes the reaction was complete, and the orange solid was filtered off on a No. 4 sinter funnel, washed with water and then dried under vacuum. The yield was 78.3%.

The NMR ($^1$H 400 MHz and $^{13}$C 100.61 MHz DMSO $d_6$) and mass spectra were in accordance with the expected structure D.

Synthesis of 2,3-diamino-5,6,7,8-tetrahydro-1H-pyrazolo[1,2-a]pyridazin-1-one hydrochloride: E 1.3 g of 3-amino-2-nitroso-5,6,7,8-tetrahydro-1H-pyrazolo[1,2-a]pyridazin-1-one (compound D) and 250 mg of 5% palladium-on-charcoal were introduced into a 300 ml autoclave containing 250 ml of ethanol. The reduction was performed with stirring at 2000 rpm, at a temperature of 60° C. and under a hydrogen pressure of 6 bar.

After reacting for 2 hours, there was no further consumption of hydrogen, and the medium was cooled to 20° C.

The catalyst was removed by filtration under nitrogen after cooling to room temperature, and the solution was poured into 75 ml of hydrochloric dioxane.

The solution thus obtained was evaporated until a slightly yellow powder was obtained, which was taken up in diisopropyl ether.

The solid was recovered by filtration. After drying under vacuum in the presence of phosphorus pentoxide, 1.1 g of 2,3-diamino-5,6,7,8-tetrahydro-1H-pyrazolo-[1,2-a]pyridazin-1-one dihydrochloride was obtained.

The NMR ($^1$H 400 MHz and $^{13}$C 100.61 MHz DMSO $d_6$) and mass spectra were in accordance with the expected structure E.

Example 7

Synthesis of 4-amino-1,2-diethyl-5-pyrrolidin-1-yl-1,2-dihydropyrazol-3-one hydrochloride

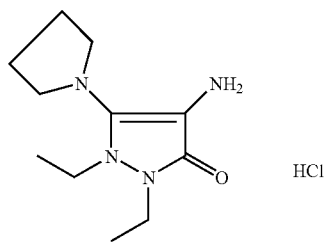

Step 1

Synthesis of 1,2-diethylpyrazolidine-3,5-dione 100 g of diethylhydrazine dihydrochloride (0.63 mol) in 1000 ml of dichloromethane, 85.3 g of malonic acid (0.82 mol; 1.3 eq.), 196 g of hydroxybenzotriazole (1.45 mol; 2.3 eq.) and 278 g of 1-(3-dimethylaminopropyl)-3-ethylcarbodiimide hydrochloride (EDCl; 1.45 mol: 2.3 eq.) were successively introduced, with magnetic stirring, into a 3000 ml three-necked flask under a nitrogen atmosphere, equipped with a thermometer.

The reaction medium was then cooled to the range of 0° C. to 5° C. 407 g of N,N-diisopropylethylamine (3.14 mol; 520 ml: 5 eq.) was then added slowly thereto. At the end of the addition, the reaction medium, which had become homogeneous, was stirred at room temperature. After leaving overnight at room temperature, the reaction was complete.

The reaction medium was washed with three times 600 ml of deionized water. The organic phase was dried over sodium sulfate, filtered and concentrated under vacuum to give 46 g of crude product. Since the pyrazolidinedione was soluble in aqueous medium, the aqueous phase was thus concentrated to dryness and then taken up in 800 ml of 1N hydrochloric acid solution. The precipitate formed was filtered off and the aqueous phase was extracted with three times 1300 ml of dichloromethane. The combined organic phases were dried over sodium sulfate, filtered and concentrated under vacuum to give 67.5 g of crude product.

1,2-Diethylpyrazolidine-3,5-dione was thus obtained in the form of a yellow solid in a yield of 40% (39.5 g).

Step 2

Synthesis of 1,2-diethyl-3-chloro-5-pyrazolone 30 g of 1,2-diethylpyrazolidine-3,5-dione (0.19 mol) dissolved in 200 ml of toluene and 35.8 ml of trichlorophosphine oxide (258.9 g; 0.38 mol; 2 eq.) were introduced, under a nitrogen atmosphere, into a 500 ml three-necked flask equipped with a condenser and a magnetic stirrer.

The reaction medium was brought to the reflux temperature of the toluene and the reaction was monitored by TLC (95/5 dichloromethane/methanol). The reaction medium, which was initially in the form of a paste, homogenized as soon as the refluxing starts and then became a two-phase mixture.

After refluxing for one hour, the reaction was hydrolysed at 0° C. by very slow addition of 100 ml of deionized water. After settling of the phases, the toluene phase was separated from the aqueous phase. The aqueous phase was washed with 50 ml of toluene and then brought to pH 12 with 184 ml of 35% sodium hydroxide solution. The formation of a precipitate was observed. The aqueous phase was maintained at 100° C. for 10 minutes and the precipitate dissolves. The reaction medium was then in two phases. The brown-colored upper phase was separated out after settling of the phases while hot. This upper phase was dissolved in 200 ml of dichloromethane, washed once with 50 ml of deionized water, dried over sodium sulfate and concentrated under vacuum to give 20.5 g of a brown oil.

A precipitate formed in the lower aqueous phase on cooling to room temperature. After filtering off through a sinter funnel, the precipitate was rinsed with water and the filtrate was extracted with three times 300 ml of dichloromethane. The dichloromethane phase was dried over sodium sulfate and concentrated under vacuum to give 5.5 g of brown crystals.

The oil and the brown crystals were collected, grafted on silica and chromatographed on silica gel (40-60 µm; 2000 g) with an elution gradient:
1) 100 dichloromethane (13 litres)
2) 99.5/0.5 dichloromethane/MeOH (0.8 litre)
3) 99/1 dichloromethane/MeOH (8 litres) expected product+ 15% impurity m=6.6 g 4) 98.5/1.5 dichloromethane/MeOH (35 litres) expected product (14.7 g).

1,2-Diethyl-3-chloro-5-pyrazolone was thus obtained in the form of yellow crystals in a yield of 44%.

Step 3

Synthesis of 1,2-diethyl-5-pyrrolidin-1-yl-1,2-dihydropyrazol-3-one

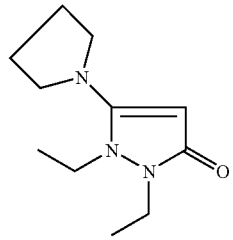

1 g of 5-chloro-1,2-diethyl-1,2-dihydropyrazol-3-one ($5.7 \times 10^{-4}$ mol) was introduced into a 2.5 ml reactor of the Biotage microwave initiator, and 2 ml of pyrrolidine (4.2 eq.) was added thereto.

The operating conditions of the microwave was at maximum power θ=120° C. for 17 minutes.

After 17 minutes, the reaction was complete (monitoring by TLC, eluent: 90/10 $CH_2Cl_2$/MeOH).

5 ml of demineralized water was then added to the reaction medium, and the assembly was then transferred into a separating funnel. The aqueous phase was extracted with four times 10 ml of dichloromethane. The organic phases were then combined and dried over anhydrous sodium sulfate, and then filtered and evaporated to dryness. 1.2 grams of a brown-orange oil were obtained in a yield of 100%.

The NMR ($^1$H 400 MHz DMSO $d_6$) and mass spectra were in accordance with the expected structure.

NMR ($^1$H 400 MHz DMSO $d_6$)

0.81 (1t, 3H), 0.89 (1t, 3H), 1.88 (1m, 1H), 3.22 (1m, 4H), 3.4 (1m, 4H), 4.4 (1s, 1H)

Mass: analysis was performed by OpenLynx (FIA/MS).

The mass mainly detected was in accordance with the expected structure: M=20.

Step 4

Synthesis of 1,2-diethyl-4-nitroso-5-pyrrolidin-1-yl-1,2-dihydro-3H-pyrazol-3-one

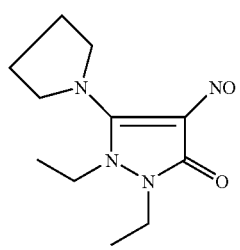

1.2 g of 1,2-diethyl-5-pyrrolidin-1-yl-1,2-dihydropyrazol-3-one was introduced into a fully equipped 25 ml three-necked flask and dissolved in a mixture composed of 0.84 ml of 37% hydrochloric acid and 4 ml of demineralized water.

The reaction medium was cooled to a range from 0° C. to 5° C. using a bath of ice-water.

A solution composed of 400 mg of sodium nitrite ($5.7 \times 10^{-4}$ mol) dissolved in 0.6 ml of demineralized water was then added dropwise.

The reaction medium immediately turned bright red as soon as the first drop of the above mixture was added.

After one hour, the reaction was complete.

The pH was adjusted to about 7-8 with 30% sodium hydroxide solution and the reaction medium was then transferred into a separating funnel. The aqueous phase was extracted with 4 times 10 ml of dichloromethane. The organic phases were combined and dried over anhydrous sodium sulfate and then evaporated to dryness. 1.2 grams of a turquoise-blue powder were obtained in a yield of 89.6%.

The NMR ($^1$H 400 MHz DMSO $d_6$) and mass spectra were in accordance with the expected structure.

NMR ($^1$H 400 MHz DMSO $d_6$) 0.94 (1t, 3H), 1 (1t, 3H), 2.05 (1m, 4H), 3.51 (1q, 4H), 3.76 (1q, 4H), 3.94 (1 m, 4H)

Analysis was performed by OpenLynx (FIA/MS).

The mass mainly detected was in accordance with the expected structure. M=238.

Step 5

Synthesis of 4-amino-1,2-diethyl-5-pyrrolidin-1-yl-1,2-dihydropyrazol-3-one hydrochloride 4 grams of zinc powder (0.06 mol) was introduced into 300 ml of absolute ethanol in a fully equipped 500 ml three-necked flask, and 1 ml of acetic acid was added thereto.

The reaction medium was heated to 40° C. and 1.15 g ($4.8 \times 10^{-3}$ mol) of 1,2-diethyl-4-nitroso-5-pyrrolidin-1-yl-1,2-dihydro-3H-pyrazol-3-one are then introduced in spatula portions. 4 ml of acetic acid was finally introduced millilitre by millilitre and the medium is brought to reflux. The medium was fully soluble and colorless. After 30 minutes, the reaction was complete on TLC according to the eluent 90/10 ethyl acetate/MeOH.

The reaction medium was cooled and then filtered on a sinter funnel containing a bed of Celite 545. The mother liquors were filtered into a round-bottomed flask containing 2.5 ml of cooled 5N hydrochloric isopropanol. The mixture was then evaporated to dryness. The product obtained was a pink powder that is in accordance by NMR and Mass.

The NMR ($^1$H 400 MHz DMSO $d_6$) and mass spectra were in accordance with the expected structure.

NMR ($^1$H 400 MHz DMSO $d_6$) 0.79 (1t, 3H), 0.96 (1t, 3H),1.87 (1m, 4H), 3.49 (1q, 2H), 3.59 (1m, 6H)

FIA/MS analysis was performed via OpenLynx.

The quasimolecular ions $[M+H]^+$, $[M+Na]^+$, $[2M+H]^+$, $[2M+Na]^+$ of the expected base $C_{11}H_{20}N_4O$ were mainly detected.

By repeating the above steps with the appropriate reagents, 4-amino-5-[3-(dimethylamino)pyrrolidin-1-yl]-1,2-diethyl-1,2-dihydro-3H-pyrazol-3-one hydrochloride may be obtained.

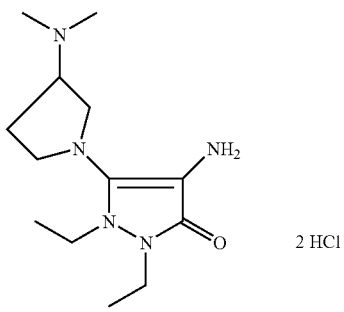

2 HCl

EXAMPLES OF DYEING

Example 1

Composition 1 below was prepared:

| | |
|---|---|
| Mixture of $C_{18}$ to $C_{24}$ linear alcohols [7/58/30/6 $C_{18}/C_{20}/C_{22}/C_{24}$, alcohol content >95%] | 3 g |
| Mixture of $C_{18}$ to $C_{24}$ oxyethylenated linear alcohols (30 EO) [7/58/30/6 $C_{18}/C_{20}/C_{22}/C_{24}$, alcohol content >95%] | 1 g |
| Oxyethylenated (2 EO) stearyl alcohol | 4.5 g |
| Oxyethylenated (21 EO) stearic acid | 1.75 g |
| 1/13 Crosslinked polyacrylic acid: | |
| CARBOPOL 980 sold by the company Goodrich | 0.6 g |
| Oleic acid | 2.6 g |
| ACULYN 22 sold by Röhm & Haas | 1.4 g AM |
| Coconut acid monoisopropanolamide | 3 g |
| Cationic polymer* | 4 g AM |
| Hexylene glycol | 6 g |
| Sodium metabisulfite | 0.71 g |
| EDTA | 0.2 g |
| tert-Butylhydroquinone | 0.3 g |
| 2,3-Diamino-6,7-dihydro-1H,5H-pyrazolo[1,2-a]-pyrazolo-1-one, HCl | 2.27 g |
| 5-Amino-6-chloro-o-cresol | 1.58 g |
| Monoethanolamine | 1 g |
| Aqueous ammonia containing 20% $NH_3$ | 11 g |
| Fragrance | qs |
| Demineralized water | qs 100 g |

*Cationic polymer consisting of the sequence of units:

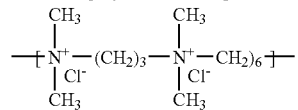

Mode of Application

At the time of use, composition 1 was mixed with 1.5 times its volume of a 25-volumes hydrogen peroxide solution, the pH of which is equal to 3. A final pH of 9.8 was obtained.

The mixture obtained was applied to locks of natural grey hair containing 90% white hairs in a proportion of 30 g of mixture per 3 g of hair. After a leave-in time of 30 minutes at room temperature, the locks were rinsed, washed with a standard shampoo, rinsed again and then dried.

The hair coloration was evaluated visually.

| | Tone depth | Tint |
|---|---|---|
| Composition 1 | Dark blond | Strong coppery |

Example 2

Composition 2 below was prepared:

| | |
|---|---|
| Mixture of $C_{18}$ to $C_{24}$ linear alcohols [7/58/30/6 $C_{18}/C_{20}/C_{22}/C_{24}$, alcohol content >95%] | 3 g |
| Mixture of $C_{18}$ to $C_{24}$ oxyethylenated linear alcohols (30 EO) [7/58/30/6 $C_{18}/C_{20}/C_{22}/C_{24}$, alcohol content >95%] | 1 g |
| Oxyethylenated (2 EO) stearyl alcohol | 4.5 g |
| Oxyethylenated (21 EO) stearic acid | 1.75 g |
| Crosslinked polyacrylic acid: | |
| Carbopol 980 sold by the company Goodrich | 0.6 g |
| Oleic acid | 2.6 g |
| Aculyn 22 sold by Röhm & Haas | 1.4 g AM |
| Coconut acid monoisopropanolamide | 3 g |
| Cationic polymer* | 4 g AM |
| Neopentyl glycol | 6 g |
| Sodium metabisulfite | 0.71 g |
| EDTA | 0.2 g |
| tert-Butylhydroquinone | 0.3 g |
| 2,3-Diamino-6,7-dihydro-1H,5H-pyrazolo[1,2-a]pyrazolo-1-one, HCl | 1.82 g |
| 2,4-diaminophenoxyethanol hydrochloride | 1.93 g |
| Monoethanolamine | 1 g |
| Aqueous ammonia containing 20% $NH_3$ | 11 g |
| Fragrance | qs |
| Demineralized water | qs 100 g |

*Idem Example 1

Mode of Application

At the time of use, composition 2 was mixed with 1.5 times its volume of a 25-volumes hydrogen peroxide solution, the pH of which is equal to 3. A final pH of 9.8 was obtained.

The mixture obtained was applied to locks of natural grey hair containing 90% white hairs, in a proportion of 30 g of mixture per 3 g of hair. After a leave-in time of 30 minutes at room temperature, the locks were rinsed, washed with a standard shampoo, rinsed again and then dried.

The hair coloration was evaluated visually.

| | Tone depth | Tint |
|---|---|---|
| Composition 2 | Light chestnut | Coppery mahogany red |

Example 3

Composition 3 below was prepared:

| | |
|---|---|
| Mixture of $C_{18}$ to $C_{24}$ linear alcohols [7/58/30/6 $C_{18}/C_{20}/C_{22}/C_{24}$, alcohol content >95%] | 3 g |
| Mixture of $C_{18}$ to $C_{24}$ oxyethylenated linear alcohols (30 EO) [7/58/30/6 $C_{18}/C_{20}/C_{22}/C_{24}$, alcohol content >95%] | 1 g |
| Oxyethylenated (2 EO) stearyl alcohol | 4.5 g |
| Oxyethylenated (21 EO) stearic acid | 1.75 g |
| Crosslinked polyacrylic acid: | |
| Carbopol 980 sold by the company Goodrich | 0.6 g |
| Oleic acid | 2.6 g |
| Aculyn 22 sold by Röhm & Haas | 1.4 g AM |
| Coconut acid monoisopropanolamide | 3 g |
| Cationic polymer* | 4 g AM |
| Hexylene glycol | 6 g |
| Sodium metabisulfite | 0.71 g |

| | |
|---|---|
| -continued | |
| EDTA | 0.2 g |
| tert-Butylhydroquinone | 0.3 g |
| 2,3-Diamino-6,7-dihydro-1H,5H-pyrazolo[1,2-a]-pyrazolo-1-one, HCl | 1.39 g |
| 5-Amino-6-chloro-o-cresol | 0.63 g |
| Monoethanolamine | 1 g |
| Citric acid | 0.15 g |
| Fragrance | qs |
| Demineralized water | qs 100 g |

*Cationic polymer consisting of the sequence of units:

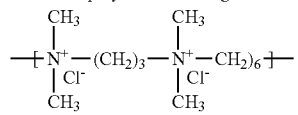

Mode of Application

At the time of use, composition 3 was mixed with 1.5 times its volume of a 25-volumes hydrogen peroxide solution, the pH of 3. A final pH of 6.85 was obtained.

The mixture obtained was applied to locks of natural grey hair containing 90% white hairs in a proportion of 30 g of mixture per 3 g of hair. After a leave-in time of 30 minutes at room temperature, the locks were rinsed, washed with a standard shampoo, rinsed again and then dried.

The hair coloration was evaluated visually.

| | Tone depth | Tint |
|---|---|---|
| Composition 3 | Light blond | Golden coppery |

What is claimed is:

1. A composition for dyeing keratin fibers, comprising, in a suitable medium:
at least one oxidation base chosen from diamino-N,N-dihydropyrazolone compounds of formula (I) and addition salts thereof:

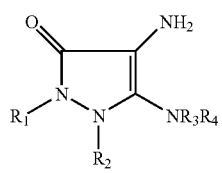

in which:
$R_1$, $R_2$, $R_3$ and $R_4$, which may be identical or different, are chosen from:
linear or branched $C_1$-$C_{10}$ alkyl radicals optionally substituted with at least one radical chosen from radicals $OR_5$, radicals $NR_6R_7$, carboxyl radicals, sulfonic radicals, carboxamido radicals $CONR_6R_7$, sulfonamido radicals $SO_2NR_6R_7$, heteroaryl or aryl radicals optionally substituted with at least one group chosen from ($C_1$-$C_4$) alkyl, hydroxyl, $C_1$-$C_2$ alkoxy, amino and (di)($C_1$-$C_2$) alkylamino groups;
aryl radicals optionally substituted with at least one radical chosen from ($C_1$-$C_4$)alkyl, hydroxyl, $C_1$-$C_2$ alkoxy, amino and (di)($C_1$-$C_2$)alkylamino radicals;
5- or 6-membered heteroaryl radicals, optionally substituted with at least one radical chosen from ($C_1$-$C_4$)alkyl and ($C_1$-$C_2$)alkoxy radicals;
$R_3$ and $R_4$ may also each be a hydrogen atom;
$R_5$, $R_6$ and $R_7$, which may be identical or different, are chosen from:
hydrogen atoms;
linear or branched $C_1$-$C_4$ alkyl radicals optionally substituted with at least one radical chosen from hydroxyl, $C_1$-$C_2$ alkoxy, carboxamido $CONR_8R_9$, sulfonyl $SO_2R_8$ and aryl radicals optionally substituted with at least one radical chosen from ($C_1$-$C_4$)alkyl, hydroxyl, $C_1$-$C_2$ alkoxy, amino and (di)($C_1$-$C_2$)alkylamino radicals; and from aryl radicals optionally substituted with at least one radical chosen from ($C_1$-$C_4$)alkyl, hydroxyl, $C_1$-$C_2$ alkoxy, amino and (di)($C_1$-$C_2$)alkylamino radicals;
$R_6$ and $R_7$, which may be identical or different, may be chosen from carboxamido radicals $CONR_8R_9$ and sulfonyl radicals $SO_2R_8$;
$R_8$ and $R_9$, which may be identical or different, are chosen from hydrogen atoms and from linear or branched $C_1$-$C_4$ alkyl radicals optionally substituted with at least one radical chosen from hydroxyl and $C_1$-$C_2$ alkoxy radicals;
$R_1$ and $R_2$, on the one hand, and $R_3$ and $R_4$, on the other hand, may form, with the nitrogen atom(s) to which they are attached, a saturated or unsaturated 5- to 7-membered heterocycle optionally substituted with at least one entity chosen from halogen atoms and amino, (di) ($C_1$-$C_4$)alkylamino, hydroxyl, carboxyl, carboxamido and ($C_1$-$C_2$)alkoxy radicals, and $C_1$-$C_4$ alkyl radicals optionally substituted with at least one radical chosen from hydroxyl, amino, (di)alkylamino, alkoxy, carboxyl and sulfonyl radicals;
$R_3$ and $R_4$ may also form, together with the nitrogen atom to which they are attached, a 5- or 7-membered heterocycle, the carbon atoms of which may be replaced with an optionally substituted oxygen or nitrogen atom;
at least one coupler; and
at least one $C_4$-$C_{30}$ polyol comprising a saturated or unsaturated, linear, branched or cyclic hydrocarbon-based chain, bearing at least two hydroxyl functions, said chain and its branches being optionally interrupted with 1 to 6 oxygen atoms and said chain and its branches being optionally substituted with at least one substituent other than hydroxyl groups, these substituents being chosen from carboxyl, amino, halogen and $C_6$-$C_{30}$ aryl groups.

2. The composition according to claim 1, wherein $R_1$ and $R_2$ are chosen from $C_1$-$C_6$ alkyl radicals optionally substituted with at least one radical chosen from hydroxyl, ($C_1$-$C_2$) alkoxy, amino, (di)($C_1$-$C_2$)alkylamino, phenyl, methoxyphenyl, ethoxyphenyl and benzyl radicals.

3. The composition according to claim 2, wherein $R_1$ and $R_2$ are independently chosen from methyl, ethyl, 2-hydroxyethyl, 3-hydroxypropyl, 2-hydroxypropyl and phenyl radicals.

4. The composition according to claim 1, wherein $R_1$ and $R_2$ form, together with the nitrogen atoms to which they are attached, a saturated or unsaturated, optionally substituted 5- or 6-membered ring.

5. The composition according to claim 1, wherein $R_1$ and $R_2$ form, together with the nitrogen atoms to which they are attached, a pyrazolidine or pyridazolidine ring, optionally substituted with at least one radical chosen from $C_1$-$C_4$ alkyl, hydroxyl, ($C_1$-$C_2$)alkoxy, carboxyl, carboxamido, amino and (di)($C_1$-$C_2$)alkylamino radicals.

6. The composition according to claims 1 wherein $R_1$ and $R_2$ form, together with the nitrogen atoms to which they are attached, a pyrazolidine or pyridazolidine ring.

7. The composition according to claim 1, wherein $R_3$ and $R_4$ are independently chosen from hydrogen atoms; linear or branched $C_1$-$C_6$ alkyl radicals optionally substituted with at least one radical chosen from hydroxyl, ($C_1$-$C_2$)alkoxy, amino and (di)($C_1$-$C_2$)alkylamino radicals; phenyl radicals optionally substituted with at least one radical chosen from hydroxyl, amino and ($C_1$-$C_2$)alkoxy radicals.

8. The composition according to claim 1, wherein $R_3$ and $R_4$ are independently chosen from hydrogen atoms and methyl, ethyl, isopropyl, 2-hydroxyethyl, 3-hydroxypropyl, 2-hydroxypropyl and 2-carboxyethyl radicals.

9. The composition according to claim 8, wherein $R_3$ and $R_4$ are both a hydrogen atom.

10. The composition according to claim 1, wherein $R_3$ and $R_4$ form, together with the nitrogen atom to which they are attached, a 5- or 7-membered ring chosen from pyrrolidine, piperidine, homopiperidine, piperazine and homopiperazine heterocycles; said rings optionally being substituted with at least one radical chosen from hydroxyl, amino, (di)($C_1$-$C_2$) alkylamino, carboxyl, carboxamido and $C_1$-$C_4$ alkyl radicals optionally substituted with at least one radical chosen from hydroxyl, amino and $C_1$-$C_2$ (di)alkylamino radicals.

11. The composition according to claim 1, wherein $R_3$ and $R_4$ form, together with the nitrogen atom to which they are attached, a 5- or 7-membered ring chosen from pyrrolidine, 2,5-dimethylpyrrolidine, pyrrolidine-2-carboxylic acid, 3-hydroxypyrrolidine-2-carboxylic acid, 4-hydroxypyrrolidine-2-carboxylic acid, 2,4-dicarboxypyrrolidine, 3-hydroxy-2-hydroxymethylpyrrolidine, 2-carboxamidopyrrolidine, 3-hydroxy-2-carboxamidopyrrolidine, 2-(diethylcarboxamido)pyrrolidine, 2-hydroxymethylpyrrolidine, 3,4-dihydroxy-2-hydroxymethylpyrrolidine, 3-hydroxypyrrolidine, 3,4-dihydroxypyrrolidine, 3-aminopyrrolidine, 3-methylaminopyrrolidine, 3-dimethylaminopyrrolidine, 4-amino-3-hydroxypyrrolidine, 3-hydroxy-4-(2-hydroxyethyl)aminopyrrolidine, piperidine, 2,6-dimethylpiperidine, 2-carboxypiperidine, 2-carboxamidopiperidine, 2-hydroxy-methylpiperidine, 3-hydroxy-2-hydroxymethyl piperidine, 3-hydroxypiperidine, 4-hydroxypiperidine, 3-hydroxymethylpiperidine, homopiperidine, 2-carboxyhomopiperidine, 2-carboxamidohomopiperidine, homopiperazine, N-methylhomopiperazine and N-(2-hydroxyethyl)homopiperazine.

12. The composition according to claim 1, wherein $R_3$ and $R_4$ form, together with the nitrogen atom to which they are attached, a 5- or 7-membered ring chosen from pyrrolidine, 3-hydroxypyrrolidine, 3-aminopyrrolidine, 3-dimethylaminopyrrolidine, pyrrolidine-2-carboxylic acid, 3-hydroxypyrrolidine-2-carboxylic acid, piperidine, hydroxy-piperidine, homopiperidine, diazepane, N-methylhomopiperazine and N-β-hydroxyethylhomopiperazine.

13. The composition according to claim 1, wherein $R_3$ and $R_4$ form, together with the nitrogen atom to which they are attached, a 5-membered ring such as pyrrolidine, 3-hydroxypyrrolidine, 3-aminopyrrolidine or 3-dimethylaminopyrrolidine.

14. The composition according to claim 1, wherein the compound of formula (I), or an addition salt thereof, is chosen from:

2,3-diamino-6,7-dihydro-1H,5H-pyrazolo[1,2-a]pyrazol-1-one;
2-amino-3-ethylamino-6,7-dihydro-1H,5H-pyrazolo[1,2-a]pyrazol-1-one;
2-amino-3-isopropylamino-6,7-dihydro-1H,5H-pyrazolo[1,2-a]pyrazol-1-one;
2-amino-3-(pyrrolidin-1-yl)-6,7-dihydro-1H,5H-pyrazolo[1,2-a]pyrazol-1-one;
4,5-diamino-1,2-dimethyl-1,2-dihydropyrazol-3-one;
4,5-diamino-1,2-diethyl-1,2-dihydropyrazol-3-one;
4,5-diamino-1,2-di-(2-hydroxyethyl)-1,2-dihydropyrazol-3-one;
2-amino-3-(2-hydroxyethyl)amino-6,7-dihydro-1H,5H-pyrazolo[1,2-a]pyrazol-1-one;
2-amino-3-dimethylamino-6,7-dihydro-1H,5H-pyrazolo[1,2-a]pyrazol-1-one;
2,3-diamino-5,6,7,8-tetrahydro-1H,6H-pyridazino[1,2-a]pyrazol-1-one;
4-amino-1,2-diethyl-5-pyrrolidin-1-yl-1,2-dihydropyrazol-3-one;
4-amino-5-(3-dimethylaminopyrrolidin-1-yl)-1,2-diethyl-1,2-dihydropyrazol-3-one;
2,3-diamino-6-hydroxy-6,7-dihydro-1H,5H-pyrazolo[1,2-a]pyrazol-1-one.

15. The composition according to claim 1, wherein the at least one coupler is chosen from meta-phenylenediamines, meta-aminophenols, meta-diphenols, naphthalene-based couplers and heterocyclic couplers, and the addition salts thereof.

16. The composition according to claim 15, wherein the at least one coupler is chosen from 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylened ioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino) toluene, and the acid-addition salts thereof.

17. The composition according to claim 15, wherein the at least one coupler is present, in an amount for each coupler, in an amount ranging from 0.001% to 10% by weight relative to the total weight of the dye composition.

18. The composition according to claim 1, wherein the at least one polyol is $C_4$-$C_{15}$.

19. The composition according to claim 1, wherein the hydrocarbon-based chain of the at least one polyol and/or its branches is interrupted with 1 to 6 oxygen atoms.

20. The composition according to claim 19, wherein the at least one polyol is chosen from polyethylene glycol containing 4, 6 or 7 ethylene units or dipropylene glycol.

21. The composition according to claim 1, wherein the hydrocarbon-based chain of the at least one polyol and its branches is not interrupted with oxygen atoms.

22. The composition according to claim 21, in which the at least one polyol is chosen from hexylene glycol; neopentyl glycol; and isoprene glycol.

23. The composition according to claim 1, in which the at least one polyol is present in an amount ranging from 0.1% to 40% by weight relative to the total weight of the dye composition.

24. The composition according to claim 1, further comprising at least one additional oxidation base chosen from para-phenylenediamines, bis(phenyl)alkylene-diamines, para-aminophenols, bis-para-aminophenols, ortho-aminophenols, ortho-phenylenediamines, and heterocyclic bases other than the derivatives of formula (I), and the addition salts thereof.

25. The composition according to claim 24, wherein the amount of the at least one additional oxidation base ranges from 0.001% to 10% by weight relative to the total weight of the dye composition.

26. The composition according to claim 1, further comprising at least one oxidizing agent.

27. A process for dyeing keratin fibers, comprising applying a dyeing composition to said keratin fibers in the presence of an oxidizing agent for a time sufficient to develop a desired coloration, wherein said dyeing composition comprises, in a suitable medium:

at least one oxidation base chosen from diamino-N,N-dihydropyrazolone compounds of formula (I) and addition salts thereof:

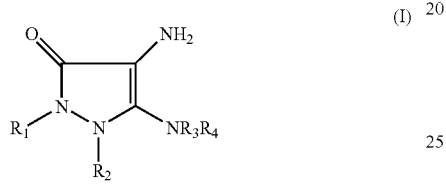

in which:

$R_1$, $R_2$, $R_3$ and $R_4$, which may be identical or different, are chosen from:

linear or branched $C_1$-$C_{10}$ alkyl radicals optionally substituted with at least one radical chosen from radicals $OR_5$, radicals $NR_6R_7$, carboxyl radicals, sulfonic radicals, carboxamido radicals $CONR_6R_7$, sulfonamido radicals $SO_2NR_6R_7$, heteroaryl or aryl radicals optionally substituted with at least one group chosen from ($C_1$-$C_4$) alkyl, hydroxyl, $C_1$-$C_2$ alkoxy, amino and (di)($C_1$-$C_2$) alkylamino groups;

aryl radicals optionally substituted with at least one radical chosen from ($C_1$-$C_4$)alkyl, hydroxyl, $C_1$-$C_2$ alkoxy, amino and (di)($C_1$-$C_2$)alkylamino radicals;

5- or 6-membered heteroaryl radicals, optionally substituted with at least one radical chosen from ($C_1$-$C_4$)alkyl and ($C_1$-$C_2$)alkoxy radicals;

$R_3$ and $R_4$ may also each be a hydrogen atom;

$R_5$, $R_6$ and $R_7$, which may be identical or different, are chosen from:

hydrogen atoms;

linear or branched $C_1$-$C_4$ alkyl radicals optionally substituted with at least one radical chosen from hydroxyl, $C_1$-$C_2$ alkoxy, carboxamido $CONR_8R_9$, sulfonyl $SO_2R_8$, aryl radicals optionally substituted with at least one radical chosen from ($C_1$-$C_4$)alkyl, hydroxyl, $C_1$-$C_2$ alkoxy, amino and (di)($C_1$-$C_2$)alkylamino radicals; and aryl radicals optionally substituted with at least one radical chosen from ($C_1$-$C_4$)alkyl, hydroxyl, $C_1$-$C_2$ alkoxy, amino and (di)($C_1$-$C_2$)alkylamino radicals;

$R_6$ and $R_7$, which may be identical or different, may be chosen from carboxamido radicals $CONR_8R_9$ and sulfonyl radicals $SO_2R_8$;

$R_8$ and $R^9$, which may be identical or different, are chosen from hydrogen atoms and from linear or branched $C_1$-$C_4$ alkyl radicals optionally substituted with at least one radical chosen from hydroxyl and $C_1$-$C_2$ alkoxy radicals;

$R_1$ and $R_2$, on the one hand, and $R_3$ and $R_4$, on the other hand, may form, with the nitrogen atom(s) to which they are attached, a saturated or unsaturated 5- to 7-membered heterocycle optionally substituted with at least one entity chosen from halogen atoms and amino, (di) ($C_1$-$C_4$)alkylamino, hydroxyl, carboxyl, carboxamido and ($C_1$-$C_2$)alkoxy radicals, and $C_1$-$C_4$ alkyl radicals optionally substituted with at least one radical chosen from hydroxyl, amino, (di)alkylamino, alkoxy, carboxyl and sulfonyl radicals;

$R_3$ and $R_4$ may also form, together with the nitrogen atom to which they are attached, a 5- or 7-membered heterocycle, the carbon atoms of which may be replaced with an optionally substituted oxygen or nitrogen atom;

at least one coupler; and at least one $C_4$-$C_{30}$ polyol comprising a saturated or unsaturated, linear, branched or cyclic hydrocarbon-based chain, bearing at least two hydroxyl functions, said chain and its branches being optionally interrupted with 1 to 6 oxygen atoms and said chain and its branches being optionally substituted with at least one substituent other than hydroxyl groups, these substituents being chosen from carboxyl, amino, halogen and $C_6$-$C_{30}$ aryl groups.

28. The process according to claim 27, wherein the oxidizing agent is chosen from hydrogen peroxide, urea peroxide, alkali metal bromates, persalts, peracids and oxidase enzymes.

29. A multi-compartment kit, wherein a first compartment comprises a dyeing composition comprising, in a suitable medium:

at least one oxidation base chosen from diamino-N,N-dihydropyrazolone compounds of formula (I) and addition salts thereof:

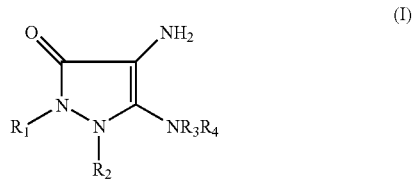

in which:

$R_1$, $R_2$, $R_3$ and $R_4$, which may be identical or different, are chosen from:

linear or branched $C_1$-$C_{10}$ alkyl radicals optionally substituted with at least one radical chosen from radicals $OR_5$, radicals $NR_6R_7$, carboxyl radicals, sulfonic radicals, carboxamido radicals $CONR_6R_7$, sulfonamido radicals $SO_2NR_6R_7$, heteroaryl or aryl radicals optionally substituted with at least one group chosen from ($C_1$-$C_4$) alkyl, hydroxyl, $C_1$-$C_2$ alkoxy, amino and (di)($C_1$-$C_2$) alkylamino groups;

aryl radicals optionally substituted with at least one radical chosen from ($C_1$-$C_4$)alkyl, hydroxyl, $C_1$-$C_2$ alkoxy, amino and (di)($C_1$-$C_2$)alkylamino radicals;

5- or 6-membered heteroaryl radicals, optionally substituted with at least one radical chosen from ($C_1$-$C_4$)alkyl and ($C_1$-$C_2$)alkoxy radicals;

$R_3$ and $R_4$ may also each be a hydrogen atom;

$R_5$, $R_6$ and $R_7$, which may be identical or different, are chosen from:

hydrogen atoms;

linear or branched $C_1$-$C_4$ alkyl radicals optionally substituted with at least one radical chosen from hydroxyl, $C_1$-$C_2$ alkoxy, carboxamido $CONR_8R_9$, sulfonyl $SO_2R_8$ and aryl radicals optionally substituted with at least one radical chosen from ($C_1$-$C_4$)alkyl, hydroxyl, $C_1$-$C_2$ alkoxy, amino and (di)($C_1$-$C_2$)alkylamino radicals; and from aryl radicals optionally substituted with at least one radical chosen from ($C_1$-$C_4$)alkyl, hydroxyl, $C_1$-$C_2$ alkoxy, amino and (di)($C_1$-$C_2$)alkylamino radicals;

$R_6$ and $R_7$, which may be identical or different, may be chosen from carboxamido radicals $CONR_8R_9$ and sulfonyl radicals $SO_2R_8$;

$R_8$ and $R_9$, which may be identical or different, are chosen from hydrogen atoms and from linear or branched $C_1$-$C_4$ alkyl radicals optionally substituted with at least one radical chosen from hydroxyl and $C_1$-$C_2$ alkoxy radicals;

$R_1$ and $R_2$, on the one hand, and $R_3$ and $R_4$, on the other hand, may form, with the nitrogen atom(s) to which they are attached, a saturated or unsaturated 5- to 7-membered heterocycle optionally substituted with at least one entity chosen from halogen atoms and amino, (di)($C_1$-$C_4$)alkylamino, hydroxyl, carboxyl, carboxamido and ($C_1$-$C_2$)alkoxy radicals, and $C_1$-$C_4$ alkyl radicals optionally substituted with at least one radical chosen from hydroxyl, amino, (di)alkylamino, alkoxy, carboxyl and sulfonyl radicals;

$R_3$ and $R_4$ may also form, together with the nitrogen atom to which they are attached, a 5- or 7-membered heterocycle, the carbon atoms of which may be replaced with an optionally substituted oxygen or nitrogen atom;

at least one coupler; and at least one $C_4$-$C_{30}$ polyol comprising a saturated or unsaturated, linear, branched or cyclic hydrocarbon-based chain, bearing at least two hydroxyl functions, said chain and its branches being optionally interrupted with 1 to 6 oxygen atoms and said chain and its branches being optionally substituted with at least one substituent other than hydroxyl groups, these substituents being chosen from carboxyl, amino, halogen and $C_6$-$C_{30}$ aryl groups, and a second compartment comprising an oxidizing agent.

* * * * *

UNITED STATES PATENT AND TRADEMARK OFFICE
CERTIFICATE OF CORRECTION

PATENT NO.       : 7,488,355 B2
APPLICATION NO.  : 11/443273
DATED            : February 10, 2009
INVENTOR(S)      : Jean-Baptiste Saunier Page 1 of 1

It is certified that error appears in the above-identified patent and that said Letters Patent is hereby corrected as shown below:

In claim 16, column 46, line 35,
"1-β-hydroxyethylamino-3,4-methylened ioxybenzene," should read
--1-β-hydroxyethylamino-3,4-methylenedioxybenzene,--.

In claim 24, column 46, line 66,
"bis(phenyl)alkylene-diamines," should read
--bis(phenyl)alkylenediamines,--.

In claim 27, column 47,
line 63, "$R^9$," should read --$R_9$,--.

Signed and Sealed this

Fourteenth Day of April, 2009

JOHN DOLL
*Acting Director of the United States Patent and Trademark Office*